(12) United States Patent
Lee et al.

(10) Patent No.: US 10,870,872 B2
(45) Date of Patent: Dec. 22, 2020

(54) ENZYMATIC NUCLEIC ACID SYNTHESIS

(71) Applicant: President and Fellows of Harvard College, Cambridge, MA (US)

(72) Inventors: Henry Hung-yi Lee, Brookline, MA (US); George M. Church, Brookline, MA (US); Reza Kalhor, East Boston, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 16/090,640

(22) PCT Filed: Mar. 30, 2017

(86) PCT No.: PCT/US2017/024939
§ 371 (c)(1),
(2) Date: Oct. 2, 2018

(87) PCT Pub. No.: WO2017/176541
PCT Pub. Date: Oct. 12, 2017

(65) Prior Publication Data
US 2019/0112626 A1    Apr. 18, 2019

Related U.S. Application Data

(60) Provisional application No. 62/317,919, filed on Apr. 4, 2016.

(51) Int. Cl.
*C12P 19/34*    (2006.01)
*C12Q 1/6844*    (2018.01)

(52) U.S. Cl.
CPC ............ *C12P 19/34* (2013.01); *C12Q 1/6844* (2013.01)

(58) Field of Classification Search
None
See application file for complete search history.

(56) References Cited

U.S. PATENT DOCUMENTS

| 4,483,964 A | 11/1984 | Urdea et al. | |
| 6,258,568 B1 * | 7/2001 | Nyren | C12Q 1/6869 |
| | | | 435/91.1 |
| 8,927,211 B2 * | 1/2015 | Turner | C12P 19/34 |
| | | | 435/6.1 |

(Continued)

OTHER PUBLICATIONS

Basu, M. et al. 'Synthesis of Compositionally Unique DNA by Terminal Deoxynucleotidyl Transferase' Biochemical and Biophysical Research Communications, 1983, vol. 111, No. 3, pp. 1105-1112; abstract.

*Primary Examiner* — Young J Kim
(74) *Attorney, Agent, or Firm* — John P. Iwanicki

(57) ABSTRACT

The disclosure provides methods for making a polynucleotide wherein the addition of nucleotides can be physically, chemically and/or enzymatically controlled. The methods include combining a selected nucleotide, cations, an error prone or template independent DNA polymerase at a reaction site including an initiator sequence attached thereto and having a 3' terminal nucleotide, wherein the reaction reagents can be modulated and under conditions that allow covalent addition of one or more of a selected nucleotide to the 3' terminal nucleotide such that the selected nucleotide becomes a 3' terminal nucleotide, and repeating the addition step until the polynucleotide is formed.

14 Claims, 17 Drawing Sheets
Specification includes a Sequence Listing.

(56) References Cited

U.S. PATENT DOCUMENTS

| | | |
|---|---|---|
| 10,745,727 B2 * | 8/2020 | Chen .................. C12Q 1/68 |
| 2010/0099080 A1 | 4/2010 | Church et al. |
| 2019/0040459 A1 | 2/2019 | Efcavitch et al. |

* cited by examiner

Initial setup

Cycling

FIG. 6 dATP analogue

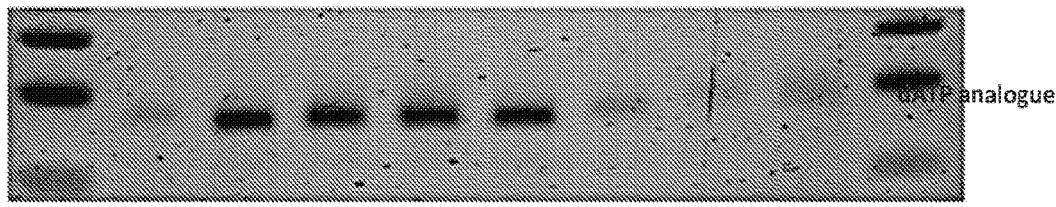

*50bp Ladder, From left to right, increasing nucleotide concentrations leads to longer extensions of initiator oligonucleotide. 50bp Ladder.* dCTP

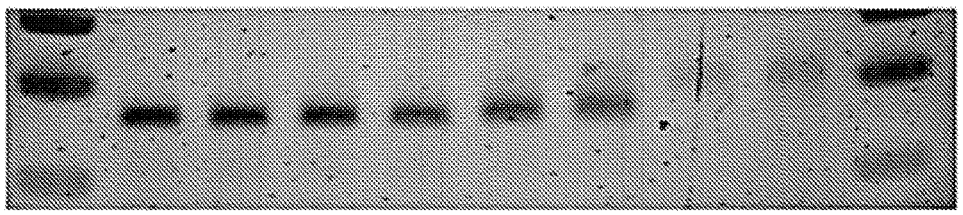

*50bp Ladder, From left to right, increasing nucleotide concentrations leads to longer extensions of initiator oligonucleotide. 50bp Ladder.* dGTP

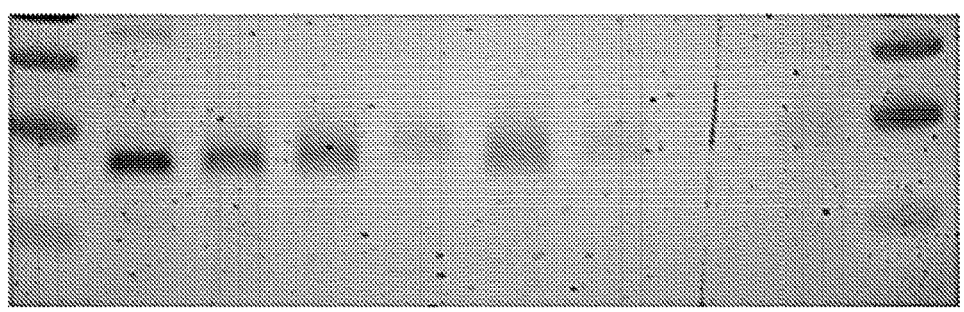

*50bp Ladder, From left to right, increasing nucleotide concentrations leads to longer extensions of initiator oligonucleotide. 50bp Ladder.* dTTP analogue

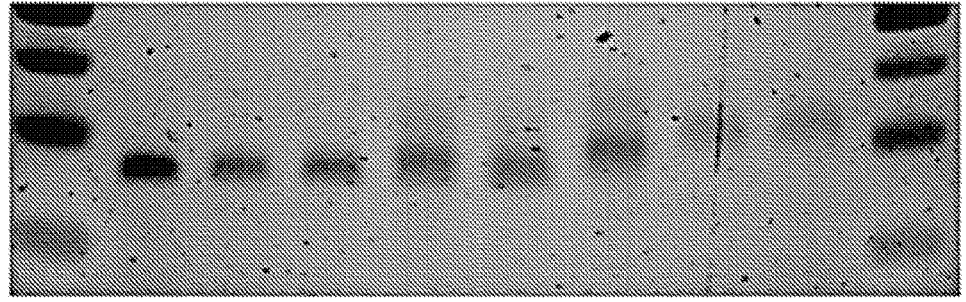

*50bp ladder. From left to right, increasing nucleotide concentrations leads to longer extensions of initiator oligonucleotide. 50bp Ladder.*

FIG. 12
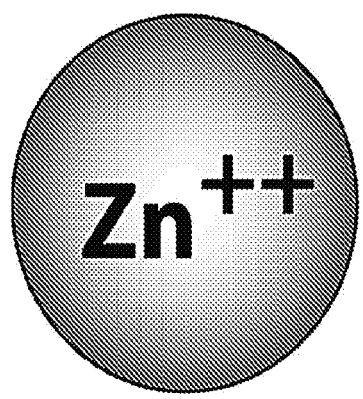
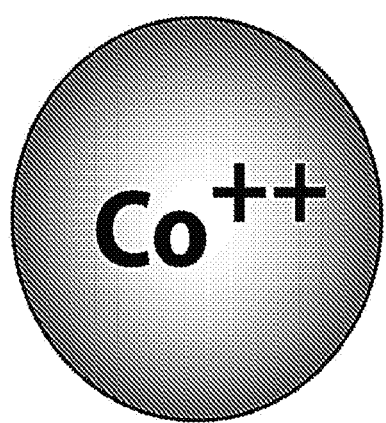
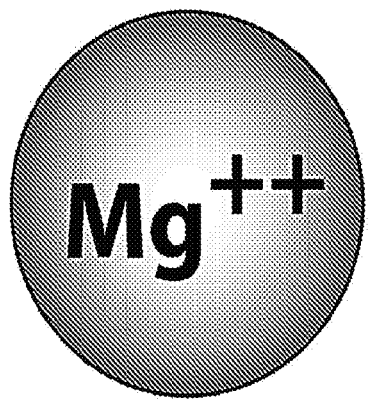
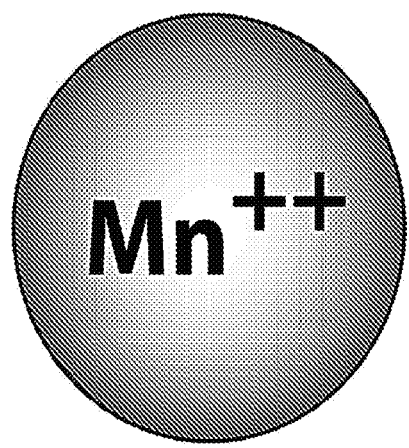

Lanes in order: pH=6, 7, 8, 9, 10, 11, non-extended initiator.

ENZYMATIC NUCLEIC ACID SYNTHESIS

RELATED APPLICATION DATA

This application is a National Stage Application under 35 U.S.C. 371 of PCT application PCT/US17/24939 designating the United States and filed Mar. 30, 2017; which claims the benefit of U.S. Provisional Application No. 62/317,919 filed on Apr. 4, 2016 which is hereby incorporated herein by reference in its entirety for all purposes.

STATEMENT OF GOVERNMENT INTERESTS

This invention was made with government support under MH103910 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Oct. 2, 2018, is named 19381040_1.txt and is 2,661 bytes in size.

FIELD

The present invention relates in general to methods of making oligonucleotides and polynucleotides using enzymatic synthesis.

BACKGROUND

DNA has been proposed as a highly desirable medium for storage of digital information. The barrier to such use of DNA is the low efficiency and speed as well as the high cost of current synthesis methods. In the current state of the art, DNA is synthesized using phosphoramidite precursors in organic solvents. These chemical synthesis methods result in errors of approximately 1% and take approximately 10 minutes per addition step. Furthermore, the reagents that are used in this synthesis process are expensive. Some of these same reagents also damage DNA, a problem that precludes the possibility of synthesizing DNA strands that are longer than ~200 bases, further hampering the efficiency of this chemical process. Despite multiple efforts, a feasible method for synthesis of custom nucleic acid sequences using terminal deoxynucleotidyl transferase (TdT) has not been described before. TdT is currently used in batch reactions for the addition of variable lengths of singular nucleotides or uncontrolled sequence of nucleotide mixtures to the 3' end of a nucleic acid sequence. A method to control the number and nature of nucleotides that TdT incorporates to generate user-defined nucleic acid sequences is a significant challenge which has not been addressed. There thus remains a need for the development of faster and cheaper enzymatic oligonucleotide synthesis methods than the existing chemical oligonucleotide synthesis methods.

SUMMARY

The present disclosure addresses this need and is based on the discovery of methods that synthesize nucleic acids of a desired sequence using a template-independent DNA polymerase. The methods according to the disclosure sequentially expose nucleic acid polymers to nucleotide polymerization units (NPUs) that extend the polymer by an expected length. The disclosure provides that each NPU comprises terminal deoxynucleotidyl transferase (TdT) and one type of nucleotide substrate (such as A, C, G, and T/U). The nucleotide substrates are in the form of nucleotide triphosphates which are the active form for polymerization purposes as contemplated by the present disclosure. The disclosure provides novel physical, chemical, and enzymatic methods to control NPU extensions and limit them to a few nucleotides. These novel methods overcome problems encountered under commonly used laboratory conditions in which NPUs would extend nucleic acid polymers indefinitely and uncontrollably. These novel methods provide sequential exposure of the DNA polymers to NPUs that contain different nucleotides and obtain nucleic acid polymers of a desired sequence, thus serving a basis for enzymatic encoding of digital information into DNA. These novel methods provide improved control of the number and nature of nucleotides that template-independent DNA polymerases, such as TdT, incorporate into nucleic acid polymers and enable user-defined synthesis of nucleic acid sequences useful for biological applications.

The most relevant enzyme for do novo synthesis of nucleic acids according to the disclosure is terminal deoxynucleotidyl transferase (TdT), a unique DNA polymerase which extends single-stranded oligonucleotides. Critically, TdT is template-independent, a property that enables the incorporation of bases into a growing strand of nucleic acids based on availability of provided nucleotides. This property makes TdT an attractive DNA polymerase for de novo DNA synthesis.

The disclosure provides that under ideal circumstances, it is desirable to limit the number of additions by TdT to one. Such DNA is not only suitable for digital information storage but also for use in biological/genetic application. The disclosure further provides that limiting the additions to one is not necessarily required for storage of information into DNA. An exemplary proper encoding strategy that, instead of considering each base as a unit of information, considers each stretch of one or more identical bases (i.e., a homopolymer) as a unit of information can be used for digital storage purposes. For instance, if every stretch of A or T represents 0 and every stretch of C or G represents 1, the sequence "AAATTAACCCCGGACTTAAGGGCC" (SEQ ID NO: 1) would be equivalent to "ATACGACTAGC" (SEQ ID NO: 2) and would represent "00011010011".

The present disclosure provides a method for making a polynucleotide comprising (a) delivering a reaction reagent mobile phase including at least an error prone template independent DNA polymerase, a selected nucleotide triphosphate and cations along a fluidic channel to a reaction site, wherein the reaction site includes an initiator attached thereto and having a 3' terminal nucleotide, wherein reaction reagents are present in the reaction reagent mobile phase at selected concentrations, wherein the reaction reagent mobile phase has a selected volume and a selected flow rate to achieve a selected residence time at the reaction site under conditions which covalently add one or more of the selected nucleotide to the 3' terminal nucleotide such that the selected nucleotide becomes a 3' terminal nucleotide, (b) delivering an organic wash mobile phase to the reaction site at a fluid flow rate to remove the reaction reagents from the reaction site, and (c) repeating steps (a) and (b) until the polynucleotide is formed, with the proviso that step (b) is not required to be performed after the polynucleotide is formed.

The present disclosure provides a method for making a polynucleotide comprising (a) combining a selected nucleotide triphosphate, cations, an error prone or template independent DNA polymerase, and a nucleotide triphosphate inactivating enzyme at a reaction site including an initiator sequence attached thereto and having a 3' terminal nucleotide, wherein reaction reagents are present at selected concentrations and under conditions which covalently add one or more of the selected nucleotide to the 3' terminal nucleotide such that the selected nucleotide becomes a 3' terminal nucleotide and under conditions which inactivate free nucleotide triphosphates until free nucleotide triphosphates are substantially inactivated, wherein a desired number of the selected nucleotide is added to the initiator sequence, and (b) repeating step (a) until the polynucleotide is formed.

The present disclosure provides a method for making a polynucleotide comprising (a) combining a selected inactive nucleotide, cations, an error prone or template independent DNA polymerase at a reaction site including an initiator sequence attached thereto and having a 3' terminal nucleotide, activating the selected inactive nucleotide, wherein reaction reagents are present at selected concentrations and under conditions which covalently add one or more of a selected activated nucleotide to the 3' terminal nucleotide such that the selected activated nucleotide becomes a 3' terminal nucleotide and under conditions wherein a desired number of the selected activated nucleotide is added to the initiator sequence, and (b) repeating step (a) until the polynucleotide is formed.

The present disclosure also provides a method for making a polynucleotide comprising (a) combining a selected nucleotide triphosphate, cations, an inactive error prone or template independent DNA polymerase at a reaction site including an initiator sequence attached thereto and having a 3' terminal nucleotide, activating the inactive error prone or template independent DNA polymerase, wherein reaction reagents are present at selected concentrations and under conditions which covalently add one or more of a selected nucleotide to the 3' terminal nucleotide such that the selected nucleotide becomes a 3' terminal nucleotide and under conditions wherein a desired number of the selected nucleotide is added to the initiator sequence, and (b) repeating step (a) until the polynucleotide is formed.

The present disclosure provides a method for making a polynucleotide comprising (a) combining a selected nucleotide triphosphate, cations, an error prone or template independent DNA polymerase at a reaction site including an initiator sequence attached thereto and having a 3' terminal nucleotide, wherein reaction reagents are present at selected concentrations and under conditions which covalently add one or more of a selected nucleotide to the 3' terminal nucleotide such that the selected nucleotide becomes a 3' terminal nucleotide and wherein the error prone or template independent DNA polymerase is inactivated to terminate addition of the selected nucleotide, and (b) repeating step (a) until the polynucleotide is formed.

The present disclosure further provides a method for making a polynucleotide comprising (a) combining a selected inactive nucleotide, cations, an inactive error prone or template independent DNA polymerase at a reaction site including an initiator sequence attached thereto and having a 3' terminal nucleotide, activating the nucleotide and activating the error prone or template independent DNA polymerase, wherein reaction reagents are present at selected concentrations and under conditions which covalently add one or more of a selected nucleotide to the 3' terminal nucleotide such that the selected nucleotide becomes a 3' terminal nucleotide, and (b) repeating step (a) until the polynucleotide is formed.

Further features and advantages of certain embodiments of the present invention will become more fully apparent in the following description of embodiments and drawings thereof, and from the claims.

BRIEF DESCRIPTION OF THE DRAWINGS

The foregoing and other features and advantages of the present embodiments will be more fully understood from the following detailed description of illustrative embodiments taken in conjunction with the accompanying drawings in which:

FIG. 1A depicts in schematic a top-down view of sequence of NPUs as they flow over the initiator oligo patch. FIG. 1B depicts in schematic a microfluidic device which implements this physical control.

FIG. 2A depicts in schematic NPU in a solution with TdT and apyrase covering an initiator oligo. FIG. 2B depicts in schematic polymerization that occurs when each base is deposited onto the NPU.

FIG. 6 depicts PCR products on Agarose gel according to the embodiments of the disclosed methods.

FIG. 12 depicts a schematic of the divalent cations that change polymerization mechanism and thereby efficiency and kinetics of polymerization.

DETAILED DESCRIPTION

Figure 1A:
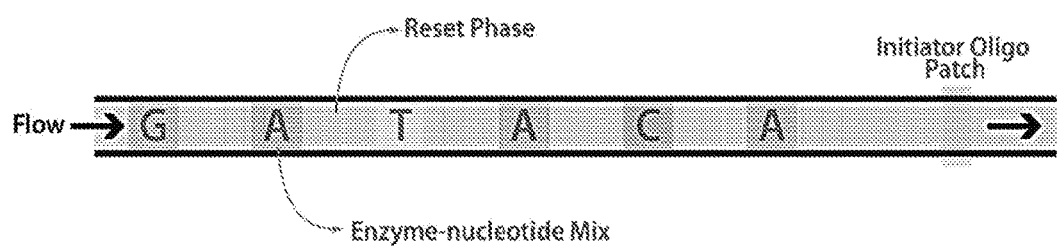
FIGS. 1A & 1B depict in schematic a physical control method of NPU exposure to nucleic acid polymers in a fluidic device.

The present disclosure provides methods of modulating activity of components and reagents used in template independent nucleic acid synthesis, such as nucleotides, template independent polymerase, and cations. The residence time of each of these components at a reaction site can be altered to modulate addition of a nucleotide to an initiator sequence or a growing nucleic acid chain. Each of these components can be activated or deactivated to modulate the addition of a nucleotide to an initiator sequence or growing nucleic acid chain. In this manner, nucleotide addition can be controlled to a desired number of nucleotides, such as one nucleotide, two nucleotides, three nucleotides etc. The disclosure provides that addition is limited to one nucleotide, two nucleotides, three nucleotides or more during one round of nucleotide addition. This activation or inactivation of the reaction components may be reversible to allow for multiple rounds of nucleotide polymerization that each adds a different nucleotide to the primer or growing polynucleotide chain.

The present disclosure provides methods of "mobile-phase oligonucleotide synthesis," an enzymatic synthesis that enables control over the number and nature of nucleotides that an error prone or template independent polymerase such as TdT adds to a primer strand of DNA, i.e., the primer/initiator for DNA synthesis. According to certain aspects of the present disclosure, the methods involve a fluidic/microfluidic device wherein initiator oligonucleotides (nucleic acids that act as the initial substrate for TdT to extend with the desired sequence) are immobilized on the surface of this device in a patch (i.e., the initiator patch). The patch is then exposed to "packets" of reagents that include TdT pre-mixed with one of the four possible nucleotide triphosphates (dNTPs). In some embodiments, the microfluidic device accurately controls the exact exposure time of the patch to each TdT-dNTP packet, thus limiting the addition to a desired count or a desired distribution of counts. In certain embodiment, the device also allows control over the order of packets, thereby enabling control over the incorporated sequence. For instance, for the synthesis of the sequence "GATC," the patch will be exposed to a packet of TdT-dGTP, followed by a packet of TdT-dATP, followed by a packet of TdT-TTP, followed by a packet of TdT-dCTP wherein the patch is exposed to each packet for an optimal time that ensures single additions or additions of a desired length or length distribution by the enzyme.

The disclosure provides a variety of ways to achieve precise control over the number of nucleotides that are added by TdT. In one embodiment, the disclosure provides "kinetic" control wherein each packet resides over the patch for a period of time long enough for a single addition but too short for two or more additions. In another embodiment, the disclosure provides combining the kinetic control with various chemical and biochemical approaches to achieve control over the number of additions of nucleotides that are added by TdT. In certain exemplary embodiments, instead of natural dNTPs, reversible terminator dNTPs can be used. Terminator dNTPs are modified dNTPs that TdT can add to a growing DNA primer but cannot extend further. In such a system, after each reversible terminator dNTP-TdT packet, a packet that reverts the termination chemically, physically, or enzymatically will also be introduced, followed by the next desired reversible terminator dNTP-TdT packet, and so on. In yet another embodiment, controlling the number of additions is achieved by using an engineered TdT or packet composition wherein the TdT enzyme remains bound to the primer at some stage in its catalytic cycle, thus blocking further additions. The next packet can allow the enzyme to complete the catalytic cycle and detach but lack any dNTPs so unwanted additions can be prevented.

The present disclosure provides that an important property of the mobile-phase synthesis strategy is that more than one liquid phase can be used in the microfluidic device. In certain embodiments, an inert organic phase, such as mineral oil, can be used to separate TdT-dNTP packets to make sure that their contents do not mix and the initiator patch is cleaned of residual content from the previous TdT-dNTP packet. An organic phase between the packets also ensures a sharp packet border and thus achieves very precise control over the exposure time of the patch to each packet. In some embodiments, the use of active chemicals in this organic phase that for instance reverse termination by terminator nucleotides is also contemplated.

The present disclosure provides that another important property of the mobile-phase synthesis strategy is that it allows a different condition to be used in each of the four TdT-dNTP packet types. This is important as the kinetics of the enzyme may be different for different dNTPs. Thus, to obtain optimal results, different conditions, such as type and concentration of divalent ions may need to be used for different dNTPs.

The present disclosure provides methods of the mobile-phase oligonucleotide synthesis which enable rapid and high-accuracy synthesis of custom DNA sequences by the template-independent DNA-polymerase terminal deoxynucleotidyl transferase (TdT). The methods according to the present disclosure can be used for synthesis of cheaper, more accurate and longer custom DNA sequences for various biochemical, biomedical, or biosynthetic applications. Furthermore, given the potential for high-speed DNA synthesis, the methods according to the present disclosure can facilitate the use of DNA as an information storage medium. In this case, a solid-phase synthesis device can be used to record digital information in DNA molecules.

Embodiments of the disclosure are directed to a method for making a polynucleotide wherein addition of the nucleotides can be physically controlled. In one embodiment, the method comprises (a) delivering a reaction reagent mobile phase including at least an error prone template independent DNA polymerase, a selected nucleotide triphosphate and cations along a fluidic channel to a reaction site, wherein the reaction site includes an initiator attached thereto and having a 3' terminal nucleotide, wherein reaction reagents are present in the reaction reagent mobile phase at selected concentrations, wherein the reaction reagent mobile phase has a selected volume and a selected flow rate to achieve a selected residence time at the reaction site under conditions which covalently add one or more of the selected nucleotide to the 3' terminal nucleotide such that the selected nucleotide becomes a 3' terminal nucleotide, (b) delivering an organic wash mobile phase to the reaction site at a fluid flow rate to remove the reaction reagents from the reaction site, and (c) repeating steps (a) and (b) until the polynucleotide is formed, with the proviso that step (b) is not required to be performed after the polynucleotide is formed.

In one embodiment, the selected volume and selected flow rate for the reaction reagent mobile phase is determined based on reactivity of the selected nucleotide triphosphate present in the reaction reagent mobile phase. In another embodiment, the selected volume and selected flow rate for the reaction reagent mobile phase differ based on the selected nucleotide triphosphate present in the reaction reagent mobile phase. In certain embodiment, the selected flow rate for the reaction reagent mobile phase is constant and the selected volume differs based on the selected nucleotide triphosphate present in the reaction reagent mobile phase. In one embodiment, the selected volume of the reaction reagent mobile phase is constant and the selected flow rate differs based on the selected nucleotide triphosphate present in the reaction reagent mobile phase. In another embodiment, the selected flow rate for the reaction reagent mobile phase is constant and the selected volume differs based on the selected nucleotide triphosphate present in the reaction reagent mobile phase and the desired number of the selected nucleotides to be added to the 3' end of the polynucleotide. In another embodiment, the selected volume of the reaction reagent mobile phase is constant and the selected flow rate differs based on the selected nucleotide triphosphate present in the reaction reagent mobile phase and the desired number of the selected nucleotides to be added to the 3' end of the polynucleotide.

In one embodiment, the reaction site is a surface area on the surface of the fluidic channel. In another embodiment, the selected concentration of reaction reagents in the reaction reagent mobile phase is determined by the selected nucleotide triphosphate present in the reaction reagent mobile phase. In another embodiment, the reaction site is within the fluidic channel. In one embodiment, the reaction site is a structure within the fluidic channel. In one embodiment, the reaction site is a collection of beads within the fluidic channel. In one embodiment, the reaction site is an electrode on the surface of the fluidic channel. In another embodiment, the reaction site is an electrode within the fluidic channel. In one embodiment, the initiator includes one or more nucleotides. In one embodiment, the residence time is sufficient to limit the number of covalent additions of the selected nucleotide.

In some embodiments, the organic wash mobile phase is immiscible with the reaction reagent mobile phase. In one embodiment, the reaction reagent mobile phase is bounded on either end by an organic wash mobile phase. In another embodiment, the organic wash mobile phase inactivates the reaction reagent mobile phase at the reaction site. In a certain embodiment, an air plug is used instead of or in addition to the organic wash mobile phase. In one embodiment, an aqueous wash mobile phase is used instead of or in addition to the organic wash mobile phase. In another embodiment, an aqueous wash mobile phase is used instead of or in addition to an air plug. In yet another embodiment, a plurality of reaction reagent mobile phases bounded on either end by an organic wash mobile phase flow to the reaction site.

The method according to the present disclosure further includes the step of monitoring covalent addition of the selected nucleotide. In one embodiment, the error prone template independent DNA polymerase is terminal deoxynucleotide transferase. In another embodiment, the cations are one or more of $Zn^{+2}$, $Co^{+2}$, $Mg^{+2}$ or $Mn^{+2}$.

The method according to the disclosure provides that the selected nucleotide is a natural nucleotide or a nucleotide analog. In some embodiments, the selected nucleotide is a member selected from the group consisting of

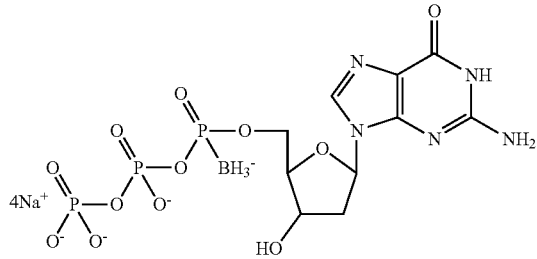

1-Borano-dATP

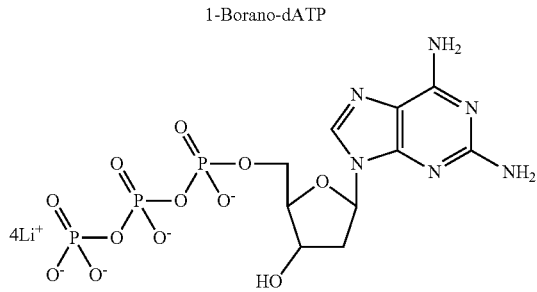

2-Amino-dATP

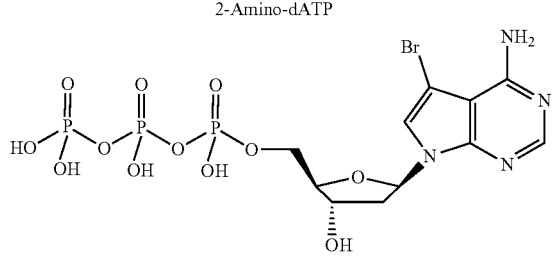

7-Deaza-7-bromo-dATP

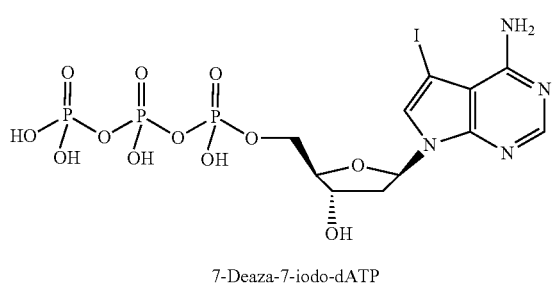

7-Deaza-7-iodo-dATP

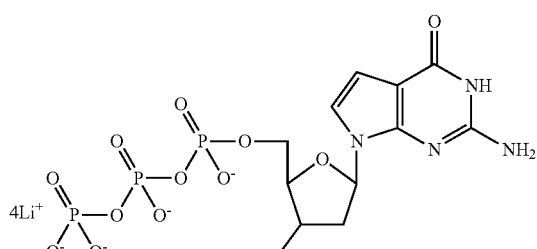

7-Deaza-dATP

-continued

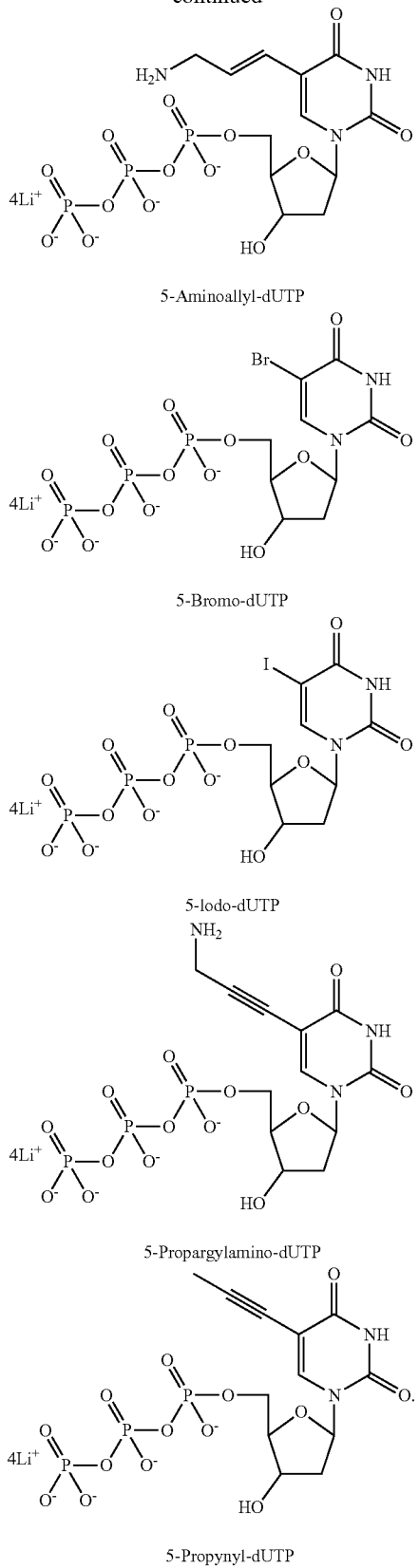

5-Aminoallyl-dUTP

5-Bromo-dUTP

5-Iodo-dUTP

5-Propargylamino-dUTP

5-Propynyl-dUTP

In one embodiment, the reaction reagent mobile phase includes a buffer comprising a monovalent salt, a divalent salt, a buffering agent, and a reducing agent at a suitable pH and temperature. In another embodiment, the reaction reagent mobile phase includes a buffer comprising 10 to 20 mM tris-acetate, 20 to 50 mM potassium acetate, 5 to 8 mM magnesium acetate, 0.5 to 1.0 mM DTT and with a pH of about 2 to 12 and at a temperature of about 10 and 80° C. In one embodiment, the reaction reagent mobile phase includes a buffer comprising 14 mM tris-acetate, 35 mM potassium acetate, 7 mM magnesium acetate, 0.7 mM DTT and with a pH of about 7.9 and at a temperature of about 25° C.

Certain embodiment of the disclosure is directed to an initiator that is attached by a cleavable moiety.

The method according to the disclosure further comprises releasing the polynucleotide from the reaction site after the desired sequence of nucleotides has been added to the 3' end of the polynucleotide. The method according to the disclosure further comprises releasing the polynucleotide from the reaction site using an enzyme, a chemical, light, heat or other suitable method or reagent. The method according to the disclosure further comprises releasing the polynucleotide from the reaction site, collecting the polynucleotide, amplifying the polynucleotide and sequencing the polynucleotide.

Embodiments of the disclosure are directed to a method for making a polynucleotide wherein the addition of nucleotides can be chemically controlled via inactivating active nucleotide triphosphates using an enzyme. In one embodiment, the method comprises (a) combining a selected nucleotide triphosphate, cations, an error prone or template independent DNA polymerase, and a nucleotide triphosphate inactivating enzyme at a reaction site including an initiator sequence attached thereto and having a 3' terminal nucleotide, wherein reaction reagents are present at selected concentrations and under conditions which covalently add one or more of the selected nucleotide to the 3' terminal nucleotide such that the selected nucleotide becomes a 3' terminal nucleotide and under conditions which inactivate free nucleotide triphosphates until free nucleotide triphosphates are substantially inactivated, wherein a desired number of the selected nucleotide is added to the initiator sequence, and (b) repeating step (a) until the polynucleotide is formed.

In one embodiment, the nucleotide inactivating enzyme is a nucleotide triphosphate degrading enzyme. In one embodiment, the nucleotide triphosphate inactivating enzyme is a nucleotide triphosphate degrading enzyme that degrades nucleotide triphosphates at a rate slower than rate of addition of nucleotides by the error prone or template independent DNA polymerase.

In certain embodiment, the nucleotide triphosphate inactivating enzyme is a nucleotide triphosphate degrading enzyme present at a concentration that degrades nucleotide triphosphates at a rate slower than rate of addition of nucleotides by the present concentration of the error prone or template independent DNA polymerase. In some embodiments, the nucleotide triphosphate inactivating enzyme comprises ATP diphosphohydrolase, dNTP pyrophosphatases, dNTPases, and phosphatases.

In one embodiment, the concentration of nucleotide triphosphate inactivating enzyme is modulated to control addition of one or more nucleotides. In one embodiment, the nucleotide triphosphate inactivating enzyme renders free nucleotide triphosphates inactive. In one embodiment, the nucleotide inactivating enzyme renders free nucleotide triphosphates inactive by degradation. In another embodiment, the nucleotide inactivating enzyme renders free nucleotide triphosphates inactive by polymerizing them with each other. In certain embodiment, the reaction conditions present a competing reaction between addition of free nucleotide triphosphates to the initiator sequence and degradation of free nucleotide triphosphates.

In one embodiment, the selected nucleotide is added to the reaction site including the initiator sequence having the terminal nucleotide, the error prone or template independent DNA polymerase and the nucleotide inactivating enzyme. In another embodiment, the error prone or template independent DNA polymerase and the nucleotide inactivating enzyme are added to the reaction site including the initiator sequence having the terminal nucleotide, and the selected nucleotide. In certain embodiment, the nucleotide inactivating enzyme is added to the reaction site including the initiator sequence having the terminal nucleotide, the error prone or template independent DNA polymerase and the selected nucleotide under conditions where the polymerase is inactive, and wherein the polymerase is activated upon addition of the nucleotide inactivating enzyme. In some embodiments, step (b) is repeated a plurality of times after which the reaction reagents are removed from the reaction site and additional reaction reagents are provided to the reaction site. In one embodiment, the reaction reagents are removed from the reaction site and additional reaction reagents are provided to the reaction site after each round of addition. In another embodiment, the reaction reagents are removed from the reaction site and additional reaction reagents are provided to the reaction site after each round of addition.

Embodiments of the disclosure are directed to a method for making a polynucleotide wherein the addition of nucleotides can be chemically controlled via activating inactive nucleotides. In one embodiment, the method comprises (a) combining a selected inactive nucleotide, cations, an error prone or template independent DNA polymerase at a reaction site including an initiator sequence attached thereto and having a 3' terminal nucleotide, activating the selected inactive nucleotide, wherein reaction reagents are present at selected concentrations and under conditions which covalently add one or more of a selected activated nucleotide to the 3' terminal nucleotide such that the selected activated nucleotide becomes a 3' terminal nucleotide and under conditions wherein a desired number of the selected activated nucleotide is added to the initiator sequence, and (b) repeating step (a) until the polynucleotide is formed.

In one embodiment, the inactive nucleotide is rendered active by a chemical reaction, an enzyme, heat, light or pH. In another embodiment, the inactive nucleotide includes a protecting group and the protecting group is removed. In some embodiments, the inactive nucleotide comprises NPE or DMNPE-caged nucleotides or similar caged nucleotides that are activated by light, heat, an enzyme, a chemical reaction, or pH. In a certain embodiment, the NPE-caged nucleotides comprise deoxynucleotide 5'-Triphosphate, P3-(1-(2-Nitrophenyl)Ethyl) esters. In a certain embodiment, the DMNPE-caged nucleotides comprise deoxynucleotide 5'-Triphosphate, P3-(1-(4,5-Dimethoxy-2-Nitrophenyl) ethyl) esters.

In one embodiment, the selected inactive nucleotide is a nucleoside, nucleotide monophosphate, or nucleotide diphosphate form that is rendered into the active nucleotide triphosphate form by an activating enzyme such as nucleotide diphosphate kinase. In another embodiment, the inactive nucleotide is rendered active at a rate which allows addition of one or more activated nucleotides. In one embodiment, the inactive nucleotide is rendered active at a rate which allows addition of one or more activated nucleotides after which either the activated nucleotides or the polymerase is rendered inactive. In another embodiment, the inactive nucleotide is rendered active allowing addition of one or more activated nucleotides after which the polymerase is rendered inactive. In yet another embodiment, the polymerase is rendered inactive by a chemical reaction, divalent cations, an enzyme, heat, light or pH.

In one embodiment, the selected inactive nucleotide is added to the reaction site including the initiator sequence having the terminal nucleotide, and the error prone or template independent DNA polymerase and the inactive nucleotide is activated. In some embodiments, step (b) is repeated a plurality of times after which the reaction reagents are removed from the reaction site and additional reaction reagents are provided to the reaction site.

Embodiments of the disclosure are directed to a method for making a polynucleotide wherein the addition of nucleotides can be chemically and enzymatically controlled via activating an inactive polymerase. In one embodiment, the method comprises (a) combining a selected nucleotide triphosphate, cations, an inactive error prone or template independent DNA polymerase at a reaction site including an initiator sequence attached thereto and having a 3' terminal nucleotide, activating the inactive error prone or template independent DNA polymerase, wherein reaction reagents are present at selected concentrations and under conditions which covalently add one or more of a selected nucleotide to the 3' terminal nucleotide such that the selected nucleotide becomes a 3' terminal nucleotide and under conditions wherein a desired number of the selected nucleotide is added to the initiator sequence, and (b) repeating step (a) until the polynucleotide is formed.

In one embodiment, the inactive error prone or template independent DNA polymerase is rendered active by a chemical reaction, divalent cations, an enzyme, heat, light or pH. In some embodiments, the inactive error prone or template independent DNA polymerase is rendered active by a chemical reaction, an enzyme, heat, light or pH and rendered inactive again by a chemical reaction, an enzyme, heat, light or pH after addition of the desired number of the selected nucleotide onto the initiator. In one embodiment, the inactive error prone or template independent DNA polymerase includes a protecting group and the protecting group is removed. In certain embodiment, the protecting group comprises a chemical group that is incorporated into the polymerase and is removable by light, heat, pH, or enzymes to control the polymerase activity.

In one embodiment, the inactive error prone or template independent DNA polymerase is rendered active at a rate which allows addition of one or more nucleotides. In another embodiment, the inactive error prone or template independent DNA polymerase is rendered active at a rate which allows addition of one or more nucleotides after which either the nucleotides or the polymerase is rendered inactive. In one embodiment, the inactive error prone or template independent DNA polymerase is rendered active allowing addition of one or more nucleotides after which the polymerase is rendered inactive. In one embodiment, the polymerase is rendered inactive by a chemical reaction, an enzyme, heat, light or pH. In certain embodiment, the inactive error prone or template independent DNA polymerase is added to the reaction site including the initiator sequence having the terminal nucleotide, and the selected nucleotide triphosphate and wherein the inactive error prone or template independent DNA polymerase is activated. In some embodiments, step (b) is repeated a plurality of times after which the reaction reagents are removed from the reaction site and additional reaction reagents are provided to the reaction site.

Embodiments of the disclosure are directed to a method for making a polynucleotide wherein the addition of nucleotides can be chemically and enzymatically controlled via inactivating active polymerase. In one embodiment, the method comprises (a) combining a selected nucleotide triphosphate, cations, an error prone or template independent DNA polymerase at a reaction site including an initiator sequence attached thereto and having a 3' terminal nucleotide, wherein reaction reagents are present at selected concentrations and under conditions which covalently add one or more of a selected nucleotide to the 3' terminal nucleotide such that the selected nucleotide becomes a 3' terminal nucleotide and wherein the error prone or template independent DNA polymerase is inactivated to terminate addition of the selected nucleotide, and (b) repeating step (a) until the polynucleotide is formed.

In one embodiment, the inactive error prone or template independent DNA polymerase is rendered active by a chemical reaction, an enzyme, heat, light or pH. In another embodiment, the active error prone or template independent DNA polymerase is rendered inactive by a chemical reaction, an enzyme, heat, light or pH after the addition of a desired number of the selected nucleotide and rendered active again by a chemical reaction, an enzyme, heat, light or pH for the addition of the next selected nucleotide to the 3' terminal nucleotide of the polynucleotide. In one embodiment, the inactive error prone or template independent DNA polymerase includes a protecting group and the protecting group is removed. In certain embodiments, the protecting group comprises a chemical group that is incorporated into the polymerase and is removable by light, heat, pH, or enzymes to control the polymerase activity.

In one embodiment, the error prone or template independent DNA polymerase is rendered inactive at a rate which allows addition of one or more nucleotides. In another embodiment, the error prone or template independent DNA polymerase is rendered inactive at a rate which allows addition of one or more nucleotides. In yet another embodiment, the error prone or template independent DNA polymerase is added to the reaction site including the initiator sequence having the terminal nucleotide, and the selected nucleotide triphosphate and wherein the error prone or template independent DNA polymerase is rendered inactive. In some embodiments, step (b) is repeated a plurality of times after which the reaction reagents are removed from the reaction site and additional reaction reagents are provided to the reaction site.

Embodiments of the disclosure are directed to a method for making a polynucleotide wherein the addition of nucleotides can be chemically and enzymatically controlled via activating the nucleotide and the polymerase. In one embodiment, the method comprises (a) combining a selected inactive nucleotide, cations, an inactive error prone or template independent DNA polymerase at a reaction site including an initiator sequence attached thereto and having a 3' terminal nucleotide, activating the nucleotide and activating the error prone or template independent DNA polymerase, wherein reaction reagents are present at selected concentrations and under conditions which covalently add one or more of a selected nucleotide to the 3' terminal nucleotide such that the selected nucleotide becomes a 3' terminal nucleotide, and (b) repeating step (a) until the polynucleotide is formed.

In one embodiment, either the active nucleotide or the active error prone or template independent DNA polymerase is rendered inactive to terminate addition of the selected nucleotide. In another embodiment, the active error prone or template independent DNA polymerase is rendered inactive by a chemical reaction, an enzyme, heat, light or pH after the addition of a desired number of the selected nucleotide and rendered active again by a chemical reaction, an enzyme, heat, light or pH for the addition of the next selected nucleotide to the 3' terminal nucleotide of the polynucleotide. In one embodiment, the inactive error prone or template independent DNA polymerase is rendered active by a chemical reaction, an enzyme, heat, light or pH. In another embodiment, the inactive error prone or template independent DNA polymerase includes a protecting group and the protecting group is removed. In some embodiments, the protecting group comprises a chemical group that is incorporated into the polymerase and is removable by light, heat, pH, or enzymes to control the polymerase activity. In one embodiment, the inactive nucleotide is rendered active by a chemical reaction, an enzyme, heat, light or pH. In another embodiment, the inactive nucleotide includes a protecting group and the protecting group is removed. In some embodiments, the inactive nucleotide comprises NPE-caged nucleotides or similar caged nucleotides that are removed by light, heat, an enzyme, a chemical reaction, or pH. In certain embodiment, the NPE-caged nucleotides comprise deoxynucleotide 5'-Triphosphate, P3-(1-(2-Nitrophenyl)Ethyl) esters. In some embodiments, the selected inactive nucleotide in a nucleoside, nucleotide monophosphate, or nucleotide diphosphate form that is rendered into the active nucleotide triphosphate form by an activating enzyme such as nucleotide diphosphate kinase. In certain embodiment, either the inactive nucleotide or inactive error prone or template independent DNA polymerase is rendered active at a rate which allows addition of one or more nucleotides. In some embodiments, step (b) is repeated a plurality of times after which the reaction reagents are removed from the reaction site and additional reaction reagents are provided to the reaction site.

Polymerases, including without limitation error-prone or template-dependent polymerases, modified or otherwise, can be used to create nucleotide polymers having a random or known or desired sequence of nucleotides. Template-independent polymerases, whether modified or otherwise, can be used to create the nucleic acids de novo. Ordinary nucleotides are used, such as A, T/U, C or G. Nucleotides may be used which lack chain terminating moieties. Reversible terminators may be used in the methods of making the nucleotide polymers. A template independent polymerase may be used to make the nucleic acid sequence. Such template independent polymerase may be error-prone which may lead to the addition of more than one nucleotide resulting in a homopolymer.

Oligonucleotide sequences or polynucleotide sequences are synthesized using an error prone polymerase, such as template independent error prone polymerase, and common or natural nucleic acids, which may be unmodified. Initiator sequences or primers are attached to a substrate, such as a silicon dioxide substrate, at various locations whether known, such as in an addressable array, or random. Reagents including at least a selected nucleotide, a template independent polymerase and other reagents required for enzymatic activity of the polymerase are applied at one or more locations of the substrate where the initiator sequences are located and under conditions where the polymerase adds one or more than one or a plurality of the nucleotide to the initiator sequence to extend the initiator sequence. The nucleotides ("dNTPs") may be applied or flow in periodic applications. Nucleotides with blocking groups or reversible terminators can be used with the dNTPs under reaction conditions that are sufficient to limit or reduce the probability of enzymatic addition of the dNTP to one dNTP, i.e. one dNTP is added using the selected reaction conditions taking into consideration the reaction kinetics. Nucleotides with blocking groups or reversible terminators are known to those of skill in the art. According to an additional embodiment when reaction conditions permit, more than one dNTP may be added to form a homopolymer run when common or natural nucleotides are used with a template independent error prone polymerase.

Polymerase activity may be modified using protease, photo-chemical or electrochemical modulation as a reaction condition so as to minimize addition of dNTP beyond a single dNTP. A wash is then applied to the one or more locations to remove the reagents. The steps of applying the reagents and the wash are repeated until desired nucleic acids are created. According to one aspect, the reagents may be added to one or more than one or a plurality of locations on the substrate in series or in parallel or the reagents may contact the entire surface of the support, such as by flowing the reagents across the surface of the support. According to one aspect, the reaction conditions are determined, for example based on reaction kinetics or the activity of the polymerase, so as to limit the ability of the polymerase to attach more than one nucleotide to the end of the initiator sequence or the growing oligonucleotide.

In addition, according to certain embodiments, polymerases can be modulated to be light sensitive for light based methods. According to this aspect, light is modulated to tune the polymerase to add only a single nucleotide. The light is shone on individual locations or pixels of the substrate where the polymerase, the nucleotide and appropriate reagents and reaction conditions are present. In this manner, a nucleotide is added to an initiator sequence or an existing nucleotide as the polymerase is activated by the light. In certain embodiments, polymerase activity can be controlled by pH. It is well known to a skilled in the art that each polymerase has an active pH range outside of which it is inactive. In one embodiment, the reaction reagent pH can adjusted in and out of the active range to control the polymerase. In an exemplary embodiment, it has been determined that TdT is active below pH 10 but is inactive at pH 11. Therefore, if the initial setup of the reaction is at pH 11, temporarily changing the pH to anywhere below 10 can temporarily activate the TdT enzyme. Furthermore, divalent cations such as Mg++, Co++, Mn++, Zn++, Ni++, are also known to a skilled in that art to be necessary for the activity of all known DNA polymerases. Chelating divalent cations from the reaction can stop the polymerase, or releasing divalent cations into the reaction can activate the polymerase. Engineered polymerases can be created which are made active by a certain wavelength of light and made inactive by another wavelength of light. Such polymerases can contain light-reactive groups such as Azobenzene, Spiropyran, or Retinal. Engineered polymerases can be made that are rendered inactive at a certain temperature but are reactivated at another. Natural polymerases are also known to have this quality but to a limited and less useful level as compared to engineered polymerases. Additionally, there exists a competitive, non-competitive, or uncompetitive chemical inhibitor of the polymerase such as Acyclovir (Zovirax) which and can be "caged" by light, pH, or heat such that it can be reversibly released/absorbed or activated/ inactivated to control the activity of the polymerase.

A flow cell or other channel, such a microfluidic channel or microfluidic channels having an input and an output is used to deliver mobile phase or reaction fluids including reagents, such as a polymerase, a nucleotide and other appropriate reagents and washes to particular locations on a substrate within the flow cell, such as within a microfluidic channel One of skill will recognize that reaction conditions will be based on dimensions of the substrate reaction region, reagents, concentrations, reaction temperature, and the structures used to create and deliver the reagents and washes. According to certain aspects, pH and other reactants and reaction conditions can be optimized for the use of TdT to add a dNTP to an existing nucleotide or oligonucleotide in a template independent manner. For example, Ashley et al., Virology 77, 367-375 (1977) hereby incorporated by reference in its entirety identifies certain reagents and reaction conditions for dNTP addition, such as initiator size, divalent cation and pH. TdT was reported to be active over a wide pH range with an optimal pH of 6.85. Methods of providing or delivering dNTP, rNTP or rNDP are useful in making nucleic acids. Release of a lipase or other membrane-lytic enzyme from pH-sensitive viral particles inside dNTP filled-liposomes is described in *J Clin Microbiol.* May 1988; 26(5): 804-807. Photo-caged rNTPs or dNTPs from which NTPs can be released, typically nitrobenzyl derivatives sensitive to 350 nm light, are commercially available from Life Technologies. Rhoposin or bacterio-opsin triggered signal transduction resulting in vesicular or other secretion of nucleotides is known in the art. With these methods for delivering dNTPs, the nucleotides should be removed or sequestered between the first primer-polymerase encountered and any downstream.

Terms and symbols of nucleic acid chemistry, biochemistry, genetics, and molecular biology used herein follow those of standard treatises and texts in the field, e.g., Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); and the like.

Nucleic Acids and Nucleotides

As used herein, the terms "nucleic acid molecule," "nucleic acid sequence," "nucleic acid fragment" and "oligomer" are used interchangeably and are intended to include, but are not limited to, a polymeric form of nucleotides that may have various lengths, including either deoxyribonucleotides or ribonucleotides, or analogs thereof.

In general, the terms "nucleic acid molecule," "nucleic acid sequence," "nucleic acid fragment," "oligonucleotide" and "polynucleotide" are used interchangeably and are intended to include, but not limited to, a polymeric form of nucleotides that may have various lengths, either deoxyribonucleotides (DNA) or ribonucleotides (RNA), or analogs thereof. A oligonucleotide is typically composed of a specific sequence of four nucleotide bases: adenine (A); cytosine (C); guanine (G); and thymine (T) (uracil (U) for thymine (T) when the polynucleotide is RNA). According to certain aspects, deoxynucleotides (dNTPs, such as dATP, dCTP, dGTP, dTTP) may be used. According to certain aspects, ribonucleotide triphosphates (rNTPs) may be used. According to certain aspects, ribonucleotide diphosphates (rNDPs) may be used.

The term "oligonucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Oligonucleotides may optionally include one or more non-standard nucleotide(s), nucleotide analog(s) and/or modified nucleotides. The present disclosure contemplates any deoxyribonucleotide or ribonucleotide and chemical variants thereof, such as methylated, hydroxymethylated or glycosylated forms of the bases, and the like. According to certain aspects, natural nucleotides are used in the methods of making the nucleic acids. Natural nucleotides lack chain terminating moieties.

Examples of modified nucleotides include, but are not limited to diaminopurine, S2T, 5-fluorouracil, 5-bromouracil, 5-chlorouracil, 5-iodouracil, hypoxanthine, xantine, 4-acetylcytosine, 5-(carboxyhydroxylmethyl)uracil, -carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, 2,6-diaminopurine and the like. Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone. Nucleic acid molecules may also contain amine-modified groups, such as aminoallyl-dUTP (aa-dUTP) and aminohexhylacrylamide-dCTP (aha-dCTP) to allow covalent attachment of amine reactive moieties, such as N-hydroxy succinimide esters (NHS).

Alternatives to standard DNA base pairs or RNA base pairs in the oligonucleotides of the present disclosure can provide higher density in bits per cubic mm, higher safety (resistant to accidental or purposeful synthesis of natural toxins), easier discrimination in photo-programmed polymerases, or lower secondary structure. Such alternative base pairs compatible with natural and mutant polymerases for de novo and/or amplification synthesis are described in Betz K, Malyshev D A, Lavergne T, Welte W, Diederichs K, Dwyer T J, Ordoukhanian P, Romesberg F E, Marx A (2012) KlenTaq polymerase replicates unnatural base pairs by inducing a Watson-Crick geometry, Nature Chem. Biol. 8:612-614; See Y J, Malyshev D A, Lavergne T, Ordoukhanian P, Romesberg F E. J Am Chem Soc. 2011 Dec. 14; 133(49):19878-88, Site-specific labeling of DNA and RNA using an efficiently replicated and transcribed class of unnatural base pairs; Switzer C Y, Moroney S E, Benner S A. (1993) Biochemistry. 32(39):10489-96. Enzymatic recognition of the base pair between isocytidine and isoguanosine; Yamashige R, Kimoto M, Takezawa Y, Sato A, Mitsui T, Yokoyama S, Hirao I. Nucleic Acids Res. 2012 March; 40(6):2793-806. Highly specific unnatural base pair systems as a third base pair for PCR amplification; and Yang Z, Chen F, Alvarado J B, Benner S A. J Am Chem Soc. 2011 Sep. 28; 133(38):15105-12, Amplification, mutation, and sequencing of a six-letter synthetic genetic system. Other non-standard nucleotides may be used such as described in Malyshev, D. A., et al., Nature, vol. 509, pp. 385-388 (15 May 2014) hereby incorporated by reference in its entirety.

Polymerases

According to an alternate embodiment of the present invention, polymerases are used to build nucleic acid molecules, such as for representing information which is referred to herein as being recorded in the nucleic acid sequence or the nucleic acid is referred to herein as being storage media. Polymerases are enzymes that produce a nucleic acid sequence, for example, using DNA or RNA as a template. Polymerases that produce RNA polymers are known as RNA polymerases, while polymerases that produce DNA polymers are known as DNA polymerases. Polymerases that incorporate errors are known in the art and are referred to herein as an "error-prone polymerases". Template independent polymerases may be error prone polymerases. Using an error-prone polymerase allows the incorporation of specific bases at precise locations of the DNA molecule. Error-prone polymerases will either accept a non-standard base, such as a reversible chain terminating base, or will incorporate a different nucleotide, such as a natural or unmodified nucleotide that is selectively given to it as it tries to copy a template. Template-independent polymerases such as terminal deoxynucleotidyl transferase (TdT), also known as DNA nucleotidylexotransferase (DNTT) or terminal transferase create nucleic acid strands by catalyzing the addition of nucleotides to the 3' terminus of a DNA molecule without a template. The preferred substrate of TdT is a 3'-overhang, but it can also add nucleotides to blunt or recessed 3' ends. Cobalt is a cofactor, however the enzyme catalyzes reaction upon Mg and Mn administration in vitro. Nucleic acid initiators may be 4 or 5 nucleotides or longer and may be single stranded or double stranded. Double stranded initiators may have a 3' overhang or they may be blunt ended or they may have a 3' recessed end.

TdT, like all DNA polymerases, also requires divalent metal ions for catalysis. However, TdT is unique in its ability to use a variety of divalent cations such as $Co^{2+}$, $Mn^{2+}$, $Zn^{2+}$ and $Mg^{2+}$. In general, the extension rate of the primer p(dA)n (where n is the chain length from 4 through 50) (SEQ ID NO: 3) with dATP in the presence of divalent metal ions is ranked in the following order: $Mg^{2+}>Zn^{2+}>Co^{2+}>Mn^{2+}$. In addition, each metal ion has different effects on the kinetics of nucleotide incorporation. For example, $Mg^{2+}$ facilitates the preferential utilization of dGTP and dATP whereas $Co^{2+}$ increases the catalytic polymerization efficiency of the pyrimidines, dCTP and dTTP. $Zn^{2+}$ behaves as a unique positive effector for TdT since reaction rates with $Mg^{2+}$ are stimulated by the addition of micromolar quantities of $Zn^{2+}$. This enhancement may reflect the ability of $Zn^{2+}$ to induce conformational changes in TdT that yields higher catalytic efficiencies. Polymerization rates are lower in the presence of $Mn^{2+}$ compared to $Mg^{2+}$, suggesting that $Mn^{2+}$ does not support the reaction as efficiently as $Mg^{2+}$. Further description of TdT is provided in Biochim Biophys Acta., May 2010; 1804(5): 1151-1166 hereby incorporated by reference in its entirety. In addition, one may replace $Mg^{2+}$, $Zn^{2+}$, $Co^{2+}$, or $Mn^{2+}$ in the nucleotide pulse with other cations designed modulate nucleotide attachment. For example, if the nucleotide pulse replaces $Mg^{++}$ with other cation(s), such as $Na^+$, $K^+$, $Rb^+$, $Be^{++}$, $Ca^{++}$, or $Sr^{++}$, then the nucleotide can bind but not incorporate, thereby regulating whether the nucleotide will incorporate or not. Then a pulse of (optional) pre-wash without nucleotide or Mg++ can be provided or then Mg++ buffer without nucleotide can be provided.

By controlling the primer/initiator, the nucleotide substrate, or the polymerase, the incorporation of specific nucleic acids into the polymer can be regulated. Thus, these polymerases are capable of incorporating nucleotides independent of the template sequence and are therefore beneficial for creating nucleic acid sequences de novo. The combination of an error-prone polymerase and a primer sequence serves as a writing mechanism for imparting information into a nucleic acid sequence.

By controlling the primer/initiator, the nucleotide substrate, or the template independent polymerase, the addition of a nucleotide to an initiator sequence or an existing nucleotide or oligonucleotide can be regulated to produce an oligonucleotide by extension. Thus, these polymerases are capable of incorporating nucleotides without a template sequence and are therefore beneficial for creating nucleic acid sequences de novo.

The eta-polymerase (Matsuda et al. (2000) Nature 404 (6781):1011-1013) is an example of a polymerase having a high mutation rate (10%) and high tolerance for 3' mismatch in the presence of all 4 dNTPs and probably even higher if limited to one or two dNTPs. Hence, the eta-polymerase is a de novo recorder of nucleic acid information similar to terminal deoxynucleotidyl transferase (TdT) but with the advantage that the product produced by this polymerase is continuously double-stranded. Double stranded DNA has less sticky secondary structure and has a more predictable secondary structure than single stranded DNA. Furthermore, double stranded DNA serves as a good support for polymerases and/or DNA-binding-protein tethers.

According to certain aspects, a template dependent or template semi-dependent error prone polymerase can be used. According to certain embodiments, a template dependent polymerase may be used which may become error prone. According to certain embodiments, a template independent RNA polymerase can be used. Where a template dependent or template semi-dependent polymerase is used, any combination of templates with universal bases can be used which encourage acceptance of many nucleotide types. In addition, error tolerant cations such as $Mn^+$ can be used. Further, the present disclosure contemplates the use of error-tolerant polymerase mutants. See Berger et al., Universal Bases for Hybridization, Replication and Chain Termination, Nucleic Acids Research 2000, Aug. 1, 28(15) pp. 2911-2914 hereby incorporated by reference. Methods of activating or inactivating template independent polymerases known to those of skill in the art are useful in the present disclosure.

Supports and Attachment

In certain exemplary embodiments, one or more oligonucleotide sequences described herein are immobilized on a support (e.g., a solid and/or semi-solid support). In certain aspects, an oligonucleotide sequence can be attached to a support using one or more of the phosphoramidite linkers described herein. Suitable supports include, but are not limited to, slides, beads, chips, particles, strands, gels, sheets, tubing, spheres, containers, capillaries, pads, slices, films, plates and the like. In various embodiments, a solid support may be biological, nonbiological, organic, inorganic, or any combination thereof. Supports of the present invention can be any shape, size, or geometry as desired. For example, the support may be square, rectangular, round, flat, planar, circular, tubular, spherical, and the like. When using a support that is substantially planar, the support may be physically separated into regions, for example, with trenches, grooves, wells, or chemical barriers (e.g., hydrophobic coatings, etc.). Supports may be made from glass (silicon dioxide), metal, ceramic, polymer or other materials known to those of skill in the art. Supports may be a solid, semi-solid, elastomer or gel. In certain exemplary embodiments, a support is a microarray. As used herein, the term "microarray" refers in one embodiment to a type of array that comprises a solid phase support having a substantially planar surface on which there is an array of spatially defined non-overlapping regions or sites that each contain an immobilized hybridization probe. "Substantially planar" means that features or objects of interest, such as probe sites, on a surface may occupy a volume that extends above or below a surface and whose dimensions are small relative to the dimensions of the surface. For example, beads disposed on the face of a fiber optic bundle create a substantially planar surface of probe sites, or oligonucleotides disposed or synthesized on a porous planar substrate create a substantially planar surface. Spatially defined sites may additionally be "addressable" in that its location and the identity of the immobilized probe at that location are known or determinable.

The solid supports can also include a semi-solid support such as a compressible matrix with both a solid and a liquid component, wherein the liquid occupies pores, spaces or other interstices between the solid matrix elements. Preferably, the semi-solid support materials include polyacrylamide, cellulose, poly dimethyl siloxane, polyamide (nylon) and cross-linked agarose, -dextran and -polyethylene glycol. Solid supports and semi-solid supports can be used together or independent of each other.

Supports can also include immobilizing media. Such immobilizing media that are of use according to the invention are physically stable and chemically inert under the conditions required for nucleic acid molecule deposition and amplification. A useful support matrix withstands the rapid changes in, and extremes of, temperature required for PCR. The support material permits enzymatic nucleic acid synthesis. If it is unknown whether a given substance will do so, it is tested empirically prior to any attempt at production of a set of arrays according to the invention. According to one embodiment of the present invention, the support structure comprises a semi-solid (i.e., gelatinous) lattice or matrix, wherein the interstices or pores between lattice or matrix elements are filled with an aqueous or other liquid medium; typical pore (or 'sieve') sizes are in the range of 100 μm to 5 nm. Larger spaces between matrix elements are within tolerance limits, but the potential for diffusion of amplified products prior to their immobilization is increased. The semi-solid support is compressible. The support is prepared such that it is planar, or effectively so, for the purposes of printing. For example, an effectively planar support might be cylindrical, such that the nucleic acids of the array are distributed over its outer surface in order to contact other supports, which are either planar or cylindrical, by rolling one over the other. Lastly, a support material of use according to the invention permits immobilizing (covalent linking) of nucleic acid features of an array to it by means known to those skilled in the art. Materials that satisfy these requirements comprise both organic and inorganic substances, and include, but are not limited to, polyacrylamide, cellulose and polyamide (nylon), as well as cross-linked agarose, dextran or polyethylene glycol.

One embodiment is directed to a thin polyacrylamide gel on a glass support, such as a plate, slide or chip. A polyacrylamide sheet of this type is synthesized as follows. Acrylamide and bis-acrylamide are mixed in a ratio that is designed to yield the degree of crosslinking between individual polymer strands (for example, a ratio of 38:2 is typical of sequencing gels) that results in the desired pore size when the overall percentage of the mixture used in the gel is adjusted to give the polyacrylamide sheet its required tensile properties. Polyacrylamide gel casting methods are well known in the art (see Sambrook et al., 1989, *Molecular Cloning. A Laboratory Manual*, 2nd Edition, Cold Spring Harbor Laboratory Press, Cold Spring Harbor, N.Y., incorporated herein in its entirety by reference), and one of skill has no difficulty in making such adjustments.

The gel sheet is cast between two rigid surfaces, at least one of which is the glass to which it will remain attached after removal of the other. The casting surface that is to be removed after polymerization is complete is coated with a lubricant that will not inhibit gel polymerization; for this purpose, silane is commonly employed. A layer of silane is spread upon the surface under a fume hood and allowed to stand until nearly dry. Excess silane is then removed (wiped or, in the case of small objects, rinsed extensively) with ethanol. The glass surface which will remain in association with the gel sheet is treated with γ-methacryloxypropyltrimethoxysilane (Cat. No. M6514, Sigma; St. Louis, Mo.), often referred to as 'crosslink silane', prior to casting. The glass surface that will contact the gel is triply-coated with this agent. Each treatment of an area equal to 1200 cm$^2$ requires 125 μl of crosslink silane in 25 ml of ethanol Immediately before this solution is spread over the glass surface, it is combined with a mixture of 750 μl water and 75 μl glacial acetic acid and shaken vigorously. The ethanol solvent is allowed to evaporate between coatings (about 5 minutes under a fume hood) and, after the last coat has dried, excess crosslink silane is removed as completely as possible via extensive ethanol washes in order to prevent 'sandwiching' of the other support plate onto the gel. The plates are then assembled and the gel cast as desired.

The only operative constraint that determines the size of a gel that is of use according to the invention is the physical ability of one of skill in the art to cast such a gel. The casting of gels of up to one meter in length is, while cumbersome, a procedure well known to workers skilled in nucleic acid sequencing technology. A larger gel, if produced, is also of use according to the invention. An extremely small gel is cut from a larger whole after polymerization is complete.

Note that at least one procedure for casting a polyacrylamide gel with bioactive substances, such as enzymes, entrapped within its matrix is known in the art (O'Driscoll, 1976, *Methods Enzymol.*, 44: 169-183, incorporated herein in its entirety by reference). A similar protocol, using photo-crosslinkable polyethylene glycol resins, that permit entrapment of living cells in a gel matrix has also been documented (Nojima and Yamada, 1987, *Methods Enzymol.*, 136: 380-394, incorporated herein in its entirety by reference). Such methods are of use according to the invention. As mentioned below, whole cells are typically cast into agarose for the purpose of delivering intact chromosomal DNA into a matrix suitable for pulsed-field gel electrophoresis or to serve as a "lawn" of host cells that will support bacteriophage growth prior to the lifting of plaques according to the method of Benton and Davis (see Maniatis et al., 1982, *Molecular Cloning: A Laboratory Manual*, Cold Spring Harbor Laboratory Press, Cold Spring Harbor, N.Y., incorporated herein in its entirety by reference). In short, electrophoresis-grade agarose (e.g., Ultrapure; Life Technologies/Gibco-BRL) is dissolved in a physiological (isotonic) buffer and allowed to equilibrate to a temperature of 50° C. to 52° C. in a tube, bottle or flask. Cells are then added to the agarose and mixed thoroughly, but rapidly (if in a bottle or tube, by capping and inversion, if in a flask, by swirling), before the mixture is decanted or pipetted into a gel tray. If low-melting point agarose is used, it may be brought to a much lower temperature (down to approximately room temperature, depending upon the concentration of the agarose) prior to the addition of cells. This is desirable for some cell types; however, if electrophoresis is to follow cell lysis prior to covalent attachment of the molecules of the resultant nucleic acid pool to the support, it is performed under refrigeration, such as in a 4° C. to 10° C. 'cold' room.

Oligonucleotides immobilized on microarrays include nucleic acids that are generated in or from an assay reaction. Typically, the oligonucleotides or polynucleotides on microarrays are single stranded and are covalently attached to the solid phase support, usually by a 5'-end or a 3'-end. In certain exemplary embodiments, probes are immobilized via one or more cleavable linkers. The density of non-overlapping regions containing nucleic acids in a microarray is typically greater than 100 per cm$^2$, and more typically, greater than 1000 per cm$^2$. Microarray technology relating to nucleic acid probes is reviewed in the following exemplary references: Schena, Editor, Microarrays: A Practical Approach (IRL Press, Oxford, 2000); Southern, Current Opin. Chem. Biol., 2: 404-410 (1998); Nature Genetics Supplement, 21:1-60 (1999); and Fodor et al, U.S. Pat. Nos. 5,424,186; 5,445,934; and 5,744,305.

Methods of immobilizing oligonucleotides to a support are known in the art (beads: Dressman et al. (2003) Proc. Natl. Acad. Sci. USA 100:8817, Brenner et al. (2000) Nat. Biotech. 18:630, Albretsen et al. (1990) Anal. Biochem. 189:40, and Lang et al. Nucleic Acids Res. (1988) 16:10861; nitrocellulose: Ranki et al. (1983) Gene 21:77; cellulose: Goldkorn (1986) Nucleic Acids Res. 14:9171; polystyrene: Ruth et al. (1987) Conference of Therapeutic and Diagnostic Applications of Synthetic Nucleic Acids, Cambridge U.K.; teflon-acrylamide: Duncan et al. (1988) Anal. Biochem. 169:104; polypropylene: Polsky-Cynkin et al. (1985) Clin. Chem. 31:1438; nylon: Van Ness et al. (1991) Nucleic Acids Res. 19:3345; agarose: Polsky-Cynkin et al., Clin. Chem. (1985) 31:1438; and sephacryl: Langdale et al. (1985) Gene 36:201; latex: Wolf et al. (1987) Nucleic Acids Res. 15:2911). Supports may be coated with attachment chemistry or polymers, such as amino-silane, NHS-esters, click chemistry, polylysine, etc., to bind a nucleic acid to the support.

As used herein, the term "attach" refers to both covalent interactions and noncovalent interactions. A covalent interaction is a chemical linkage between two atoms or radicals formed by the sharing of a pair of electrons (i.e., a single bond), two pairs of electrons (i.e., a double bond) or three pairs of electrons (i.e., a triple bond). Covalent interactions are also known in the art as electron pair interactions or electron pair bonds. Noncovalent interactions include, but are not limited to, van der Waals interactions, hydrogen bonds, weak chemical bonds (i.e., via short-range noncovalent forces), hydrophobic interactions, ionic bonds and the like. A review of noncovalent interactions can be found in Alberts et al., in Molecular Biology of the Cell, 3d edition, Garland Publishing, 1994.

According to certain aspects, affixing or immobilizing nucleic acid molecules to the substrate is performed using a covalent linker that is selected from the group that includes oxidized 3-methyl uridine, an acrylyl group and hexaethylene glycol. In addition to the attachment of linker sequences to the molecules of the pool for use in directional attachment to the support, a restriction site or regulatory element (such as a promoter element, cap site or translational termination signal), is, if desired, joined with the members of the pool. Nucleic acids that have been synthesized on the surface of a support may be removed, such as by a cleavable linker or linkers known to those of skill in the art. Linkers can be designed with chemically reactive segments which are optionally cleavable with agents such as enzymes, light, heat, pH buffers, and redox reagents. Such linkers can be employed to pre-fabricate an in situ solid-phase inactive reservoir of a different solution-phase primer for each discrete feature. Upon linker cleavage, the primer would be released into solution for PCR, perhaps by using the heat from the thermocycling process as the trigger.

It is also contemplated that affixing of nucleic acid molecules to the support is performed via hybridization of the members of the pool to nucleic acid molecules that are covalently bound to the support.

Immobilization of nucleic acid molecules to the support matrix according to the invention is accomplished by any of several procedures. Direct immobilizing via the use of 3'-terminal tags bearing chemical groups suitable for covalent linkage to the support, hybridization of single-stranded molecules of the pool of nucleic acid molecules to oligonucleotide primers already bound to the support, or the spreading of the nucleic acid molecules on the support accompanied by the introduction of primers, added either before or after plating, that may be covalently linked to the support, may be performed. Where pre-immobilized primers are used, they are designed to capture a broad spectrum of sequence motifs (for example, all possible multimers of a given chain length, e.g., hexamers), nucleic acids with homology to a specific sequence or nucleic acids containing variations on a particular sequence motif. Alternatively, the primers encompass a synthetic molecular feature common to all members of the pool of nucleic acid molecules, such as a linker sequence.

Two means of crosslinking a nucleic acid molecule to a polyacrylamide gel sheet will be discussed in some detail. The first (provided by Khrapko et al., 1996, U.S. Pat. No. 5,552,270) involves the 3' capping of nucleic acid molecules with 3-methyl uridine. Using this method, the nucleic acid molecules of the libraries of the present invention are prepared so as to include this modified base at their 3' ends. In the cited protocol, an 8% polyacrylamide gel (30:1, acrylamide: bis-acrylamide) sheet 30 µm in thickness is cast and then exposed to 50% hydrazine at room temperature for 1 hour. Such a gel is also of use according to the present invention. The matrix is then air dried to the extent that it will absorb a solution containing nucleic acid molecules, as described below. Nucleic acid molecules containing 3-methyl uridine at their 3' ends are oxidized with 1 mM sodium periodate (NaIO4) for 10 minutes to 1 hour at room temperature, precipitated with 8 to 10 volumes of 2% $LiClO_4$ in acetone and dissolved in water at a concentration of 10 pmol/µl. This concentration is adjusted so that when the nucleic acid molecules are spread upon the support in a volume that covers its surface evenly and is efficiently (i.e., completely) absorbed by it, the density of nucleic acid molecules of the array falls within the range discussed above. The nucleic acid molecules are spread over the gel surface and the plates are placed in a humidified chamber for 4 hours. They are then dried for 0.5 hour at room temperature and washed in a buffer that is appropriate to their subsequent use. Alternatively, the gels are rinsed in water, re-dried and stored at −20° C. until needed. It is thought that the overall yield of nucleic acid that is bound to the gel is 80% and that of these molecules, 98% are specifically linked through their oxidized 3' groups.

A second crosslinking moiety that is of use in attaching nucleic acid molecules covalently to a polyacrylamide sheet is a 5' acrylyl group, which is attached to the primers. Oligonucleotide primers bearing such a modified base at their 5' ends may be used according to the invention. In particular, such oligonucleotides are cast directly into the gel, such that the acrylyl group becomes an integral, covalently bonded part of the polymerizing matrix. The 3' end of the primer remains unbound, so that it is free to interact with, and hybridize to, a nucleic acid molecule of the pool and prime its enzymatic second-strand synthesis.

Alternatively, hexaethylene glycol is used to covalently link nucleic acid molecules to nylon or other support matrices (Adams and Kron, 1994, U.S. Pat. No. 5,641,658). In addition, nucleic acid molecules are crosslinked to nylon via irradiation with ultraviolet light. While the length of time for which a support is irradiated as well as the optimal distance from the ultraviolet source is calibrated with each instrument used due to variations in wavelength and transmission strength, at least one irradiation device designed specifically for crosslinking of nucleic acid molecules to hybridization membranes is commercially available (Stratalinker, Stratagene). It should be noted that in the process of crosslinking via irradiation, limited nicking of nucleic acid strands occurs. The amount of nicking is generally negligible, however, under conditions such as those used in hybridization procedures. In some instances, however, the method of ultraviolet crosslinking of nucleic acid molecules will be unsuitable due to nicking. Attachment of nucleic acid molecules to the support at positions that are neither 5'- nor 3'-terminal also occurs, but it should be noted that the potential for utility of an array so crosslinked is largely uncompromised, as such crosslinking does not inhibit hybridization of oligonucleotide primers to the immobilized molecule where it is bonded to the support.

Supports described herein may have one or more optically addressable virtual electrodes associated therewith such that an anion toroidal vortex can be created at a reaction site on the supports described herein.

Reagent Delivery Systems

According to certain aspects, reagents and washes are delivered that the reactants are present at a desired location for a desired period of time to, for example, covalently attached dNTP to an initiator sequence or an existing nucleotide attached at the desired location. A selected nucleotide reagent liquid is pulsed or flowed or deposited at the reaction site where reaction takes place and then may be optionally followed by delivery of a buffer or wash that does not include the nucleotide. Suitable delivery systems include fluidics systems, microfluidics systems, syringe systems, ink jet systems, pipette systems and other fluid delivery systems known to those of skill in the art. Various flow cell embodiments or flow channel embodiments or microfluidic channel embodiments are envisioned which can deliver separate reagents or a mixture of reagents or washes using pumps or electrodes or other methods known to those of skill in the art of moving fluids through channels or microfluidic channels through one or more channels to a reaction region or vessel where the surface of the substrate is positioned so that the reagents can contact the desired location where a nucleotide is to be added.

According to another embodiment, a microfluidic device is provided with one or more reservoirs which include one or more reagents which are then transferred via microchannels to a reaction zone where the reagents are mixed and the reaction occurs. Such microfluidic devices and the methods of moving fluid reagents through such microfluidic devices are known to those of skill in the art.

Immobilized nucleic acid molecules may, if desired, be produced using a device (e.g., any commercially-available inkjet printer, which may be used in substantially unmodified form) which sprays a focused burst of reagent-containing solution onto a support (see Castellino (1997) *Genome Res.* 7:943-976, incorporated herein in its entirety by reference). Such a method is currently in practice at Incyte Pharmaceuticals and Rosetta Biosystems, Inc., the latter of which employs "minimally modified Epson inkjet cartridges" (Epson America, Inc.; Torrance, Calif.). The method of inkjet deposition depends upon the piezoelectric effect, whereby a narrow tube containing a liquid of interest (in this case, oligonucleotide synthesis reagents) is encircled by an adapter. An electric charge sent across the adapter causes the adapter to expand at a different rate than the tube, and forces a small drop of liquid reagents from the tube onto a coated slide or other support.

Reagents can be deposited onto a discrete region of the support, such that each region forms a feature of the array. The feature is capable of generating an anion toroidal vortex as described herein. The desired nucleic acid sequence can be synthesized drop-by-drop at each position, as is true for other methods known in the art. If the angle of dispersion of reagents is narrow, it is possible to create an array comprising many features. Alternatively, if the spraying device is more broadly focused, such that it disperses nucleic acid synthesis reagents in a wider angle, as much as an entire support is covered each time, and an array is produced in which each member has the same sequence (i.e., the array has only a single feature).

The following examples are set forth as being representative of the present disclosure. These examples are not to be construed as limiting the scope of the present disclosure as these and other equivalent embodiments will be apparent in view of the present disclosure, figures and accompanying claims.

EXAMPLES

Exemplary embodiments of the present disclosure are directed to methods of enzymatic synthesis of user-defined nucleic acid sequences using TdT. The methods according to the present disclosure contemplate four major parts: physical and chemical control of nucleic acid polymer exposure to NPU, nucleotide analogue substrates for TdT, conditions for TdT polymerization, and finally, an example implementation of our inventions for TdT-based NPUs to synthesize nucleic acids of a defined information content. These novel methods according to the present disclosure can be used for the synthesis of nucleic acid polymers for information storage in DNA. These novel methods according to the present disclosure further provide improved control of the number and nature of nucleotides that template-independent DNA polymerases, such as TdT, incorporate into nucleic acid polymers and enable user-defined synthesis of nucleic acid sequences useful for biological applications.

Controlled NPU Exposure to Nucleic Acid Polymers

The present disclosure provides that limiting the number of nucleotide additions by TdT can be achieved by controlling one or a combination of the following three elements of the polymerization reaction: the primer/initiator, the nucleotide substrate, or the polymerase. Previous and ongoing attempts at custom DNA synthesis using TdT focus on the primer/initiator combined with the nucleotide. Specifically, others have tried using reversible-terminator nucleotide analogs to synthesize DNA of a desired sequence. However, it has been found that TdT does not efficiently work with any of the available reversible terminator nucleotide analogues. Furthermore, using such analogues adds to both the cost and complexity of DNA synthesis while increasing synthesis time. The present disclosure provides novel methods of enzymatic synthesis that focus on controlling the nucleotide and the polymerase, i.e., the NPU, using various physical and chemical control approaches.

Figure 1B:
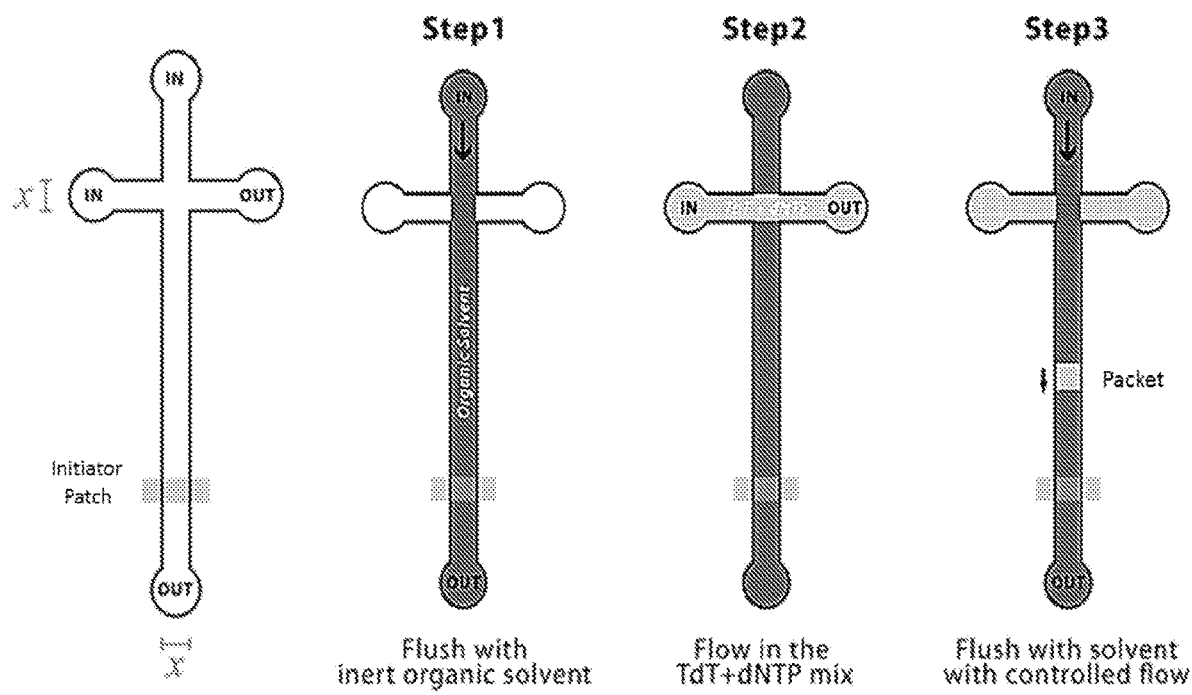

In one approach according to the methods of the present disclosure, the time the initiator/primer is in physical contact with NPU is controlled. In one embodiment, the method of the disclosure provides an efficient way to establish such a physical method of NPU exposure control through fluidics. An exemplary embodiment of such a method is shown in FIGS. 1A and 1B, in which initiator oligonucleotides were immobilized on a surface of a fluidic device (called initiator patch or patch). The patch is then exposed to NPUs which include TdT pre-mixed with only one of the four possible nucleotide triphosphates (dNTPs). As shown in FIG. 1B, the microfluidic device flows each NPU over the patch at a given rate, thus limiting the exposure time of the patch to each NPU to generate an extension of a desired base to a desired count or desired distribution of counts. In certain embodiments, the device also allows control over the order of NPUs, thereby allowing control over the incorporated sequence and information content (FIG. 1A). For instance, for the synthesis of the sequence "GATC," the patch will be serially exposed to four NPUs. The NPUs will each includes TdT with dGTP, dATP, dTTP, and dCTP, respectively. The fluidic control exposes the patch to each of the NPUs for the optimal time which ensures addition of that specific nucleotide to the entire patch of initiator oligonucleotides.

Figure 2A:
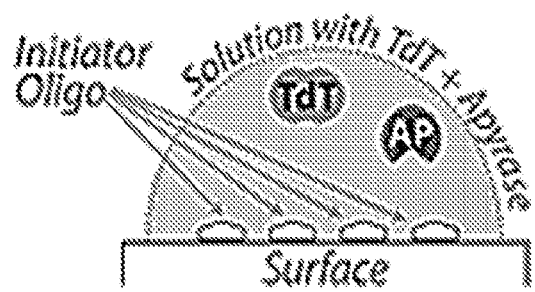
FIGS. 2A & 2B depict in schematic a chemical control method of NPU exposure to nucleic acid polymers in a fluidic device.
Figure 2B:
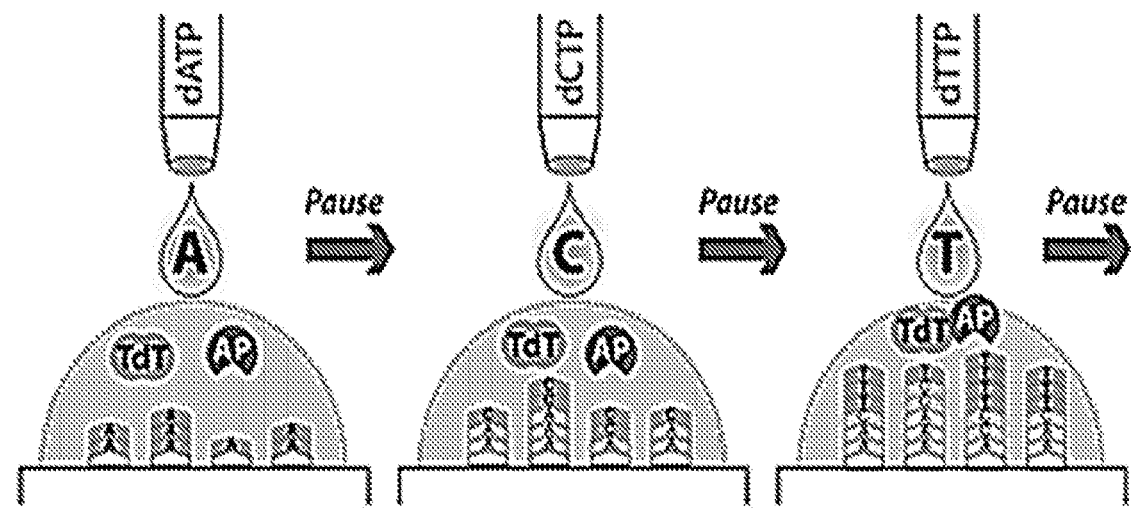

In another approach according to the methods of the present disclosure, the amount of time the nucleotide substrates are available to the enzyme for extension of the primer/initiator is controlled. In one embodiment, the enzyme "ATP diphosphohydrolase" (Apyrase), which degrades dNTPs, was added to a reaction with TdT (FIG. 2A). This addition results in two competing reactions: one is the polymerization of free nucleotides by TdT to a nucleic acid polymer and the other is the degradation of free nucleotides available to TdT by Apyrase. The concentration of Apyrase was optimized which allowed reproducible addition of nucleotide extensions of set lengths. Once a nucleotide was added to the initiator by the polymerase and its excess was degraded by apyrase, the next nucleotide would be added to the mixture (FIG. 2B). For instance, for the synthesis of the sequence "GATC," the initiator, TdT, and apyrase were mixed. Then a small amount of dGTP was added to this mix. After a few seconds, once TdT has extended the initiators and apyrase has degraded the excess dGTP, a small amount of dATP would be added to the mix. So on, a few seconds later dTTP would be added. dCTP would be added a few seconds after that. This new control strategy obviated the challenging requirement for high temporal exposure control presented in the first physical control approach.

The methods of the present disclosure contemplate additional approaches beyond these two specific examples that provide similar control over exposure of primer/initiator to the NPU. In some embodiments, these additional approaches include: activating inactive nucleotides or inactive TdT enzyme by heat, wavelengths of light, or pH, and using a protease to remove the TdT enzyme as opposed to removing the dNTPs by apyrase from the reaction after a set amount of time, etc.

Nucleotide Analogue Substrates for TdT

In the general scheme of the presently disclosed methods, the distribution of extension length by TdT is important to ensure efficient and reliable encoding of information into DNA. It has been found that the extension efficiency, rate, and extension length distribution of each of the four natural nucleotides (A, C, G, and T) was different. In fact, it has been observed that dCTP shows the most optimal behavior while dATP and dTTP show the poorest behavior with respect to TdT-based DNA synthesis. Given these observations, several nucleotide analogues were screened to search for nucleotide analogues with a superior performance compared to their natural counterparts in TdT-based DNA synthesis. The following nucleotide analogues with the NPU formulation which included Apyrase were explored.

TABLE 1

Screened nucleotide analogues.

| dATP analogues | dTTP analogues | dGTP analogues |
|---|---|---|
| 1-Borano-dATP | dUTP | d7-Deaza-dGTP |
| 1-Thio-dATP | Aminoallyl-dUTP | 1-Borano-dGTP |
| 2-Amino-dATP | 5-Br-dUTP | 1-Thio-dGTP |
| N6-Methyl-dATP | 5-Fluoro-dUTP | |
| 7-Deaza-dATP | 5-Iodo-dUTP | |
| 8-Chloro-dATP | 5-HydroxyM-dUTP | |
| 8-Oxo-dATP | 5-Aminoallyl-dUTP | |
| | 5-Propynyl-dUTP | |
| | 5-Propargylamino-dUTP | |
| | 5-Bromo-dUTP | |

Figure 3:
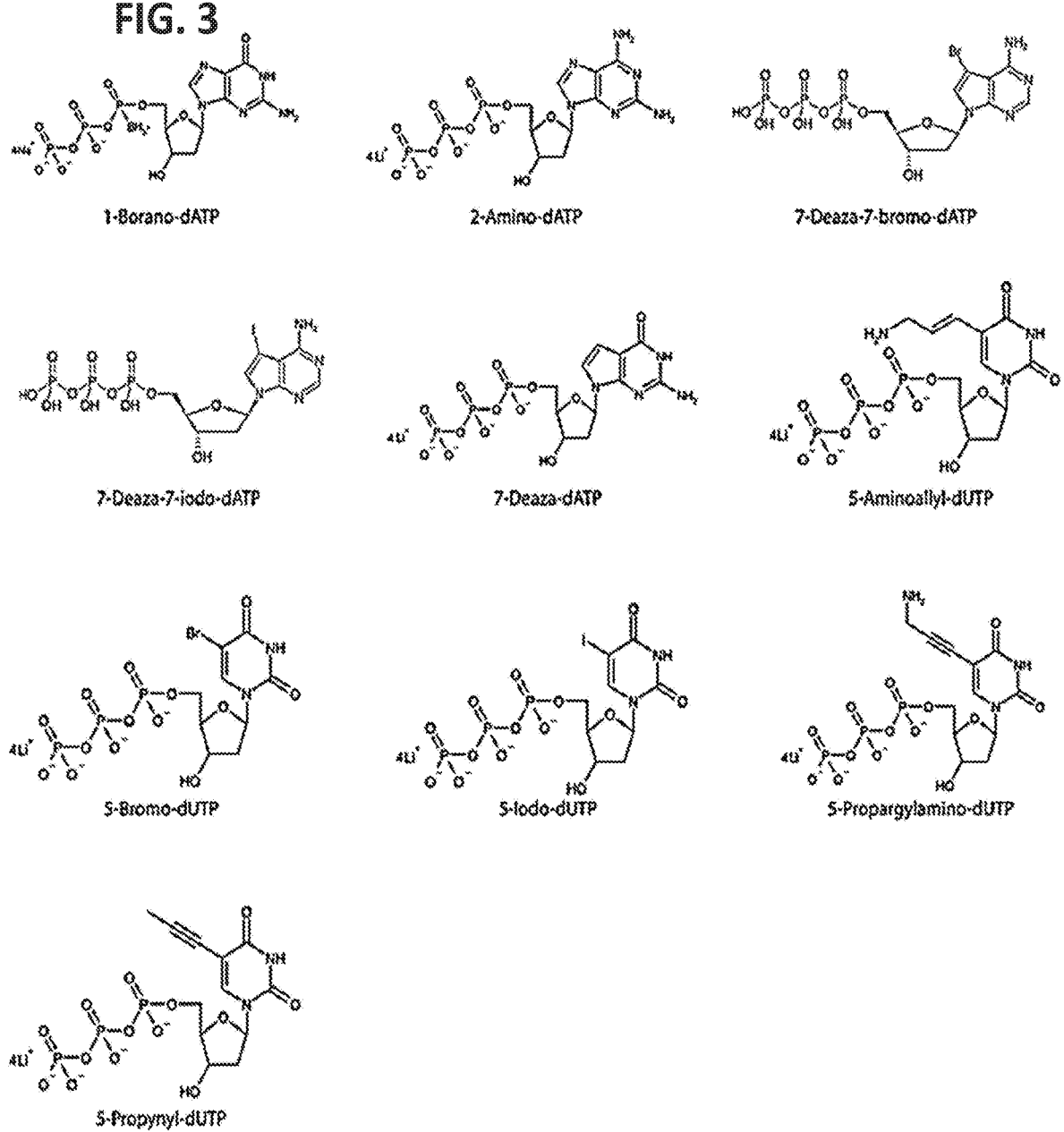
FIG. 3 depicts screened nucleotide analog substrates for TdT to select for better performance on extension efficiency, rate, and extension length distribution according to the embodiments of the disclosed methods.

It has been found that the following nucleotide analogues displayed equally good or superior efficiency, rate, and/or length distribution compared to their natural counterparts with TdT (see FIG. 3 for nucleotide structures).

TABLE 2

Improved dATP alternatives.

7-Deaza-7-bromo-dATP
1-Borano-dATP (2'-Deoxyadenosine-5'-O-(1-Boranotriphosphate))
2-Amino-dATP (Diaminopurine)
7-Deaza-dATP
7-Deaza-7-iodo-dATP

TABLE 3

Improved dTTP alternatives.

5-propynyl-dUTP
5-Bromo-dUTP
5-Iodo-dUTP
5-Aminoallyl-dUTP
5-Propargylamino-dUTP In general, it has been observed that all nucleotide analogues that are more positively charged than their natural counterparts are far more efficient substrates of TdT. These analogues include, but are not limited to, 5-Aminoallyl-dUTP and 5-Propargylamino-dUTP.

Additional nucleotide analogues within the scope of the present disclosure include

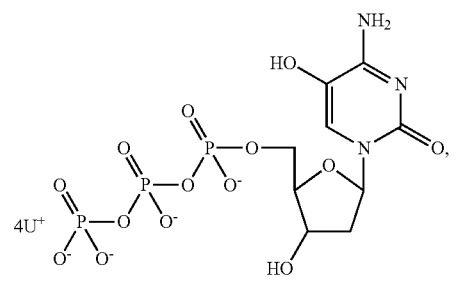

1-5-Hydroxy-dCTP (hdCTP)

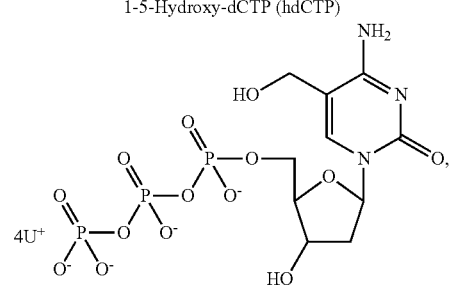

2-5-Hydroxymethyl-dCTP (hmdCTP)

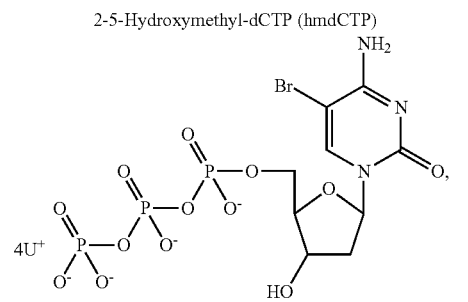

3-5-Bromo-dCTP (BrdCTP)

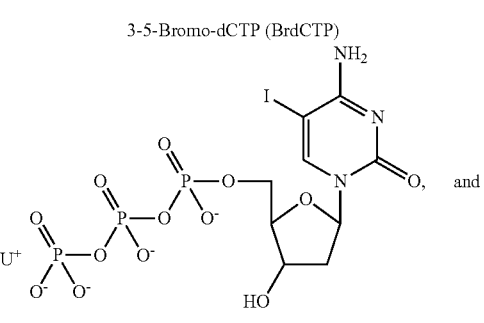

4-5-Iodo-dCTP (IdCTP)

and

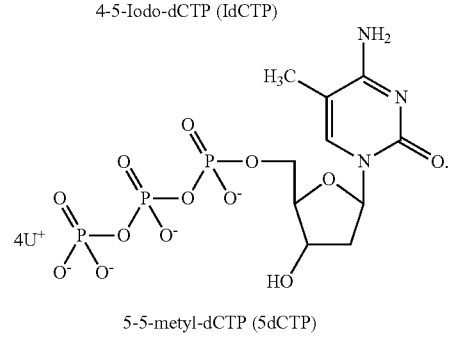

5-5-metyl-dCTP (5dCTP)

Biochemical Formulations for Controlled TdT Synthesis

It has been found that the following buffer formula is optimal for TdT polymerization, allowing efficient addition of all nucleotides by TdT:

10 to 20 mM Tris-Acetate
20 to 50 mM Potassium Acetate 5 to 8 mM Magnesium Acetate
0.5-1.0 mM DTT
pH 7.9 in 25° C.

Apyrase is also active in above conditions.

Specifically, it has been found the following buffer to be most optimal for TdT polymerization:
14 mM Tris-Acetate
35 mM Potassium Acetate
7 mM Magnesium Acetate
0.7 mM DTT
pH 7.9 in 25° C.

Apparatus Implementation

Figure 4:
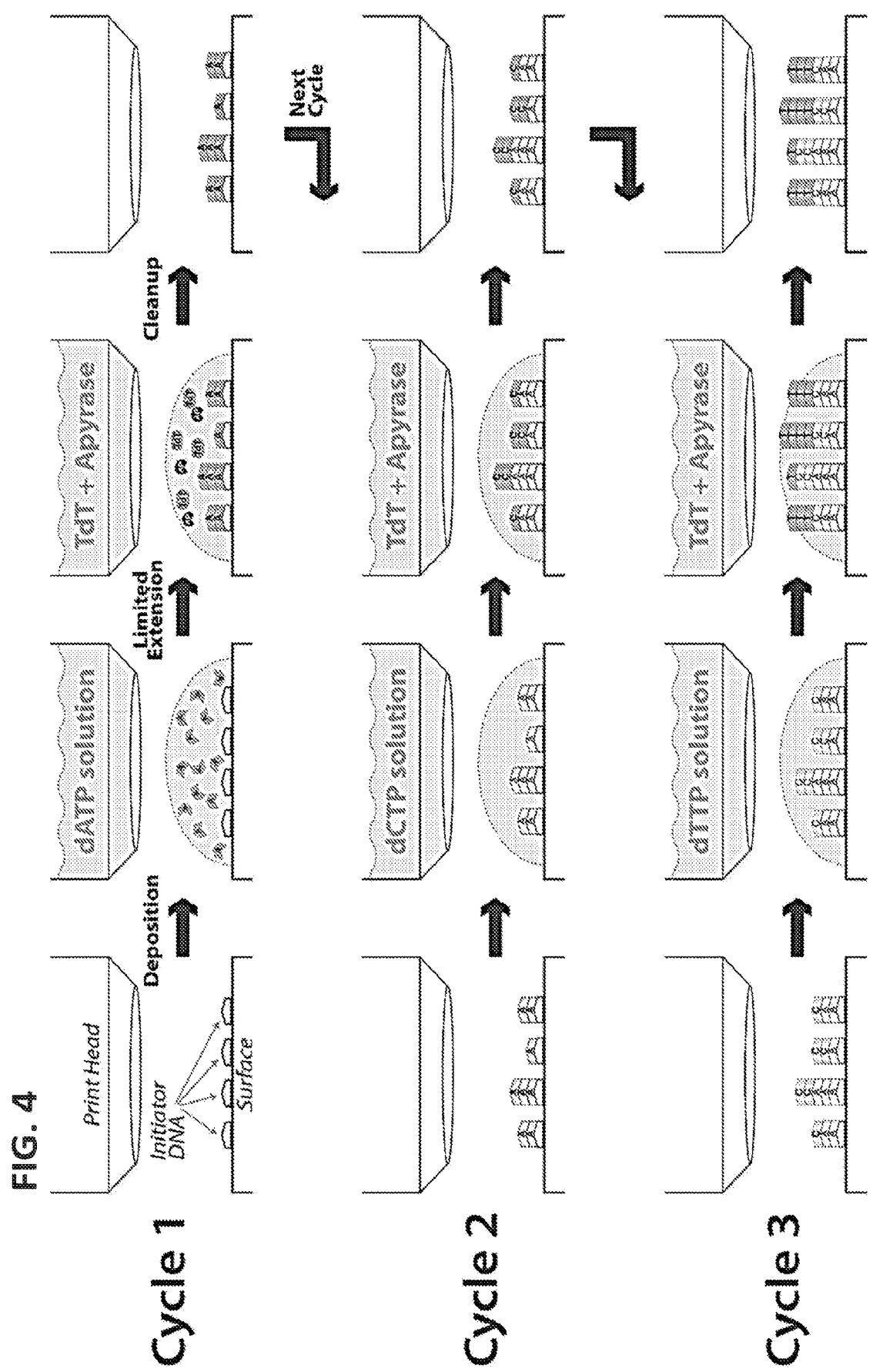
FIG. 4 depicts in schematic an apparatus which implements certain embodiments of the disclosed methods for TdT-based NPU synthesis of DNA with given information content. Initiator DNA is immobilized to a glass surface and the desired nucleotide is deposited on the DNA. NPUs including TdT and apyrase are deposited to catalyze a limited extension. After cleanup, the oligo is ready for the deposition of the next nucleotide and NPUs.

The present disclosure provides exemplary apparatus, protocol, and implementation of a method of NPU enzymatic synthesis to generate a nucleic acid polymer of a given information content. An embodiment of this implementation is illustrated in FIG. 4. Each of the four NPUs is a formulation of TdT, Apyrase, and one of the following nucleotides: 7-Deaza-7-bromo-dATP, dCTP, dGTP, and 7-propynyl-dUTP.

A robotic dispensing system (Mantis Robot from the company Formulatrix) which can be programmed to reproducibly move in xyz space and to dispense liquids at 100 nanoliter increments was used. Using this robot, 100 nanoliters of initiator oligos were deposited on ArrayIt SuperAldehyde2 coated slides (Cat. SMA2F) at an optimal concentration between 0.04 micromolar and 5 micromolar, and resuspended in 1× Microspotting solution (ArrayIt). The initiator oligos were designed with a 5 prime amine modification for immobilization to the glass surface and with deoxyUridines to enable oligo release by USER (Uracil-Specific Excision Reagent) Enzyme as seen:

```
5Am12-fS3-ctgac:
/5AmMC12/TTTTTTTTT/ideoxyU//ideoxyU/
CTACACTCTTTCCCTACACGACGCTCTTCCGATCT CTGAC (SEQ ID
NO: 4)
```

The slides with the initiator oligos were incubated with 1.4× Microspotting solution (ArrayIt) and 500 millimolar NaCl (3.5 mililiter 2× oligo spotting solution, 1 mililiter water, 0.5 mililiter of a 5 molar NaCl solution) for 24 hours in a closed environment to prevent evaporation. The slides were then dried first at room temperature then incubated at 60° C. for 1 hour. The slide were then washed once with water, once with 0.1% SDS+1 millimolar Tris HCl at pH 8.0, and three more times with water (with vigorous shaking the last time).

To reduce the Schiff bases and unreacted aldehydes, a solution of 0.15 g $NaBH_4$ in 35 mililiter PBS was prepared. After $NaBH_4$ was dissolved, 15 mililiter 100% ethanol was added to the solution. The slides were incubated in this solution for 15 minutes with tube cap left open to allow the hydrogen gas to escape. The slides were then washed with water twice.

To denature DNA, the slides were incubated in 80° C. water for three minutes and then submerged in ice-cold 100% ethanol for thirty seconds (last sequence to denature the oligos and keep them that way). The slides were ready to be used for enzymatic synthesis once dried by centrifugation at 500 g for 3 minutes in a conical tube.

The following cycling procedure is used to synthesize DNA of a given information content:
1. 0.2 microliters of the desire nucleotide resuspended in 25% ethanol (or other solvents that could speed up evaporation while maintaining the nucleotide's solubility) was deposited on the oligo spot and dried at room temperature (this takes a couple of minutes).
2. 0.5-1 microliters of the NPU (formulation below) was deposited on each oligo spot with the dried nucleotide:
Water: 7.5 microliter
3.5× GreenBuffer: 2 microliter
TdT:Apyrase Stock (1 U: 1 mU): 0.5 microliter
Total Volume: 10 microliter
3. Following incubation at room temperature, the spot was washed with room temperature 0.1% SDS once, water twice, and once dried, was ready for step 1 of the cycling procedure.

Once the sequence has been synthesized, a DNA adapter was ligated to the 3 prime end of the extended oligos. Ligation was carried out on the slides overnight at room temperature by flooding the slide surface with the following mixture in a sealed container to prevent moisture and oxygen:

| | |
|---|---|
| 10 microliter | 10X T4 RNA Ligase Buffer (NEB) |
| 10 microliter | 10 millimolar ATP |
| 50 microliter | 50% PEG 8K |
| 10 microliter | 5P-cagtc-rS9-dd (10 micromolar) |
| 8 microliter | T4 RNA Ligase |
| 12 microliter | water |
| 100 microliter | Total Volume |

5P-cagtc-rS9-dd/5phos/CAGTC AGATCG-GAAGAGCACACGTCTGAACTCCAGTCA/3ddC/(SEQ ID NO: 5)

This ligation mixture was washed off the slides by 0.1% SDS wash and two washes with water and subsequently dried by ligation.

Samples can be eluted by depositing 1 microliter of the following USER mix:

| | |
|---|---|
| 42.5 microliter | 10 millimolar Tris + 0.001% Tween20 |
| 5 microliter | UDG (2 U/ul) |
| 2.5 microliter | EndoVIII (10 U/ul) |
| 50 microliter | Total Volume |

After incubation at 37° C. for 30 minutes, the samples were transferred to independent tubes and diluted with 50 microliter of a 10 millimolar Tris+0.001% Tween20 solution. 5 microliters of each reaction was quantified in quantitative PCR with the appropriate primers such as:

```
f-tS3  CTACACTCTTTCCCTACACGAC (SEQ ID NO: 6)

f-ttS9 GTGACTGGAGTTCAGACGTG  (SEQ ID NO: 7)
``` which could then be amplified appropriately for high-throughput sequencing platforms known to a skilled in the art, including but not limited to Illumina, Pacific Bioscience, or Oxford Nanopore.

An Experimental Protocol Summary for Physical Control

Materials and Methods

According to an exemplary protocol of the present disclosure, an initiator oligonucleotide was first immobilized onto a surface called the initiator patch, in this exemplary embodiment by UV crosslinking DNA to glass surface. After tethering the initiator to a solid support, the surface was treated to neutralize the chemical reactive groups such as aldehydes in this case, and to increase hydrophobicity. A pre-fabricated custom PDMS device was subsequently plasma treated in order to covalently attach it to the glass slide with the initiator patch.

Nitrogen pumps were used to push aqueous slugs, i.e. discrete volumes, containing the enzymatic cocktail, through one channel and oil slugs, i.e. discrete volumes, containing the wash solution, through the other channel. The pump rates were adjusted to give roughly 100 micron long slugs of the aqueous phase separated by roughly 1 millimeter long slugs of organic phase. The residence time of each aqueous slug on the initiator patch was adjusted by altering the pump rates, while keeping the relative rates of the aqueous channel and oil pumps the same. The total reaction time was the sum of all residence times of each aqueous slug passing over the initiator patch while the pumps are active.

After each desired reaction time, the synthesized DNA on the initiator patch can be assessed for the number of nucleotides added. By imaging, the length of nucleotides added can be assessed by the use of fluorescent nucleotides or hybridization of fluorescent probes. The synthesized DNA on the initiator patch can also be released, in this exemplary embodiment, enzymatically, by the use of USER (Uracil-Specific Excision Reagent) enzyme which cleaves the uracils that are near the 5 prime distal end of the initial initiator oligonucleotide. The cleaved DNA strands are then collected by flow into a tube. These strands are subsequently PCR amplified and the number of synthesized nucleotides evaluated by two methods: electrophoresis on agarose or PAGE gels for cursory bulk analysis and sequenced with next-generation sequencing platforms such as Illumina, Pacific Bioscience, and/or Oxford Nanopore for quantitative single-molecule analysis.

Detailed Protocol

1. Glass slides were washed with 1M HCl for 10 minutes with shaking, rinsed twice with ultrapure water, washed with acetone for 5 minutes while shaking, and air dried.

2. On the backside of the glass slides, a marker was used to mark the placement spot for the initiator oligo. Oligo ctgac was diluted to 5 uM in PBS. 3 uL of this oligo solution was placed on the glass slides and incubated at 60° C. until dry.

```
                                                    (SEQ ID NO: 8)
ctgac
TTTTTTTTTTTTTTTTTTTTTTTTTTTT/ideoxyU//ideoxyU/CGA
CGCTCTTCCGATCTCTGAC
```

3. Using a UV Stratalinker 2400, the oligo was covalently attached to the glass by exposure to 100 uJ for 6.5 seconds. The slides were then washed with 0.1×SSC with 0.2% SDS for 5 minutes with shaking, rinsed once with water and dried at 60° C. for 10 min.

Figure 5:
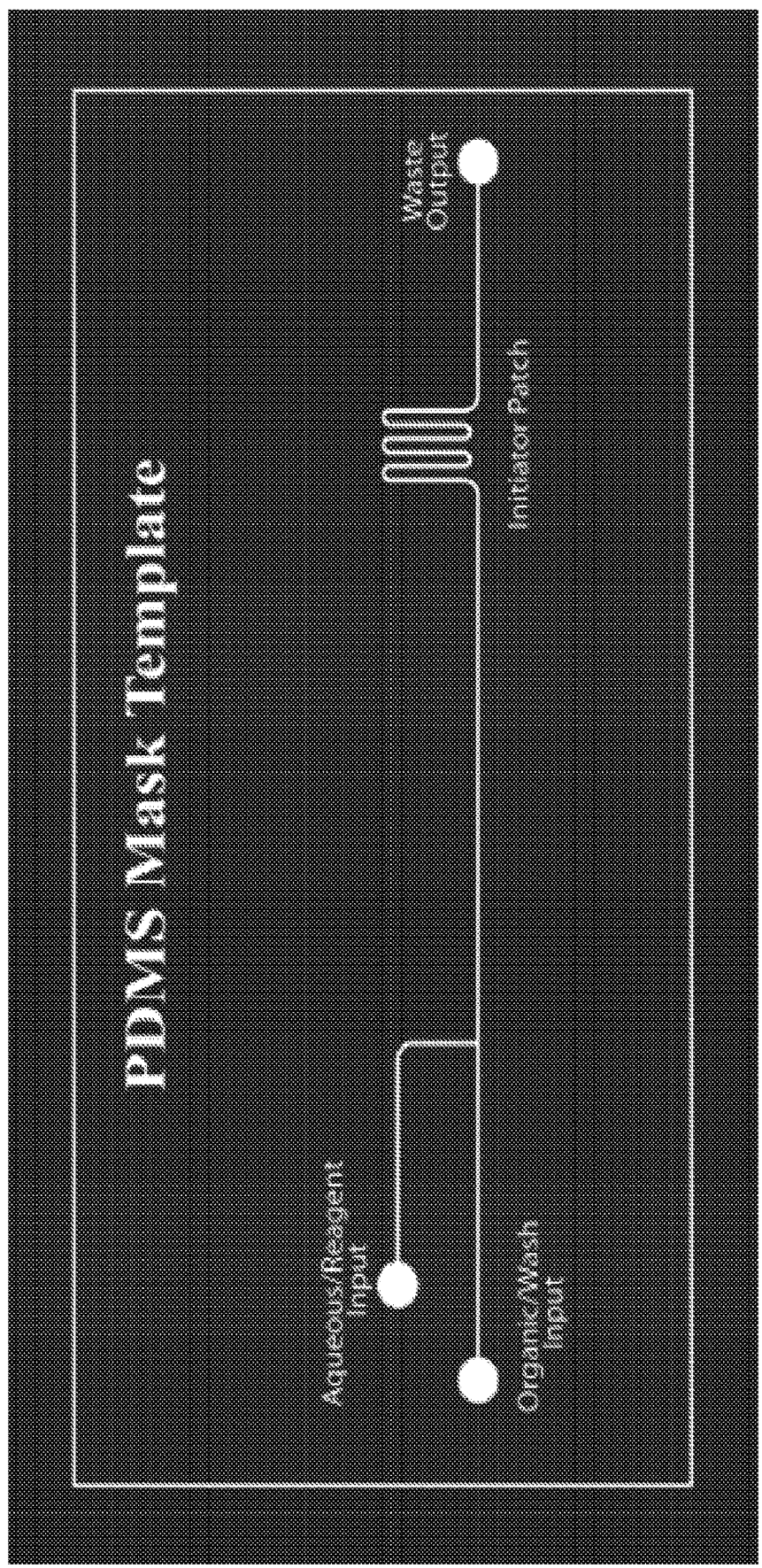
FIG. 5 depicts in schematic a PDMS mask template for generating a microfluidic device which implements the physical control of NPU exposure to nucleic acid polymers.

4. A PDMS mask with, previously casted to contain a 100 micron channel with a standard T junction (illustration in FIG. 5) was treated with Oxygen Plasma at 200 milliwatts for 30 seconds and sealed onto the glass slides such that the oligo patch would be under the part of the channel that was intended for the initiator.

5. The organic phase was a 7 to 3 mixture of Hexadecane and AR-20 Silicon Oil (both obtained from Sigma). An air pump was used to continuously pump this organic/wash solution in the device through the Organic/Wash Input with a back pressure of 10 Mega Pascals.

6. The aqueous reagent was prepared with the following composition:

15 mM Tris-Acetate, 35 mM Potassium Acetate, 7 mM Magnesium Acetate, 1 U/uL TdT enzyme, 0.01% Triton X-100, 1 mM Cy5-dATP, pH=8.0.

Another airpump was used to continuously pump this aqueous reagent solution through the Aqueous/Reagent Input on the device.

7. As a result, roughly 100 micron long slugs of the aqueous phase separated by roughly 1 millimeter long slugs of organic phase were constantly generated. The total residence time of these aqueous slugs on the initiator patch could be increased or decreased by respectively increasing or decreasing the total pump-generated pressure in the system. The number of slugs that came in contact with the initiator patch could be controlled by the total time that the pumps were on.

8. At the end of the experiment the channel was washed with 2×SSC.

9. The amount of polymerization on the initiator patch was assessed by imaging the initiator patch of the device in Cy5 channel using an inverted fluorescence microscope.

The results of this experiment showed that the average number of nucleotides added to the initiator by each slug, as measured by total fluorescence intensity, can be controlled by changing the exposure time of the initiator patch to each slug.

An Experimental Protocol Summary for Chemical Control Materials and Methods

According to an exemplary protocol of the present disclosure, an initiator oligonucleotide was first immobilized onto a surface, for example with the use of a 5 prime modified oligonucleotide onto aldehyde functionalized glass slides. After tethering the initiator to a solid support, the surface was treated to neutralize the chemical reactive groups such as aldehydes in this case, and to increase hydrophobicity.

Dilutions of nucleotides in solvents such as water or ethanol of the following concentration and types were prepared:

0, 15.625, 31.25, 62.5, 125, 250, 500, and 1000 uM dilutions of 7-deaza-7-bromo-dATP, 7-propynyl-dUTP, dCTP, and dGTP.

Each of these nucleotides were printed on an oligo spot with a liquid handling robot followed by printing of the enzymatic mix comprising TdT (Terminal deoxynucleotidyl transferase) and Apyrase. After a specified reaction time between the oligonucleotide, printed nucleotide, and print enzymatic mix, the slides were washed and a terminal oligonucleotide was ligated onto the synthesized DNA to allow for subsequent amplification.

Each of the synthesized DNA strands were released off the solid-support surface, in this exemplary embodiment, enzymatically, by the use of USER (Uracil-Specific Excision Reagent) enzyme which cleaves the uracils that are near the 5 prime distal end of the initial initiator oligonucleotide. These strands were subsequently PCR amplified and the number of synthesized nucleotides were evaluated by two methods: electrophoresis on agarose or PAGE gels for cursory bulk analysis and sequenced with next-generation sequencing platforms such as Illumina, Pacific Bioscience, and/or Oxford Nanopore for quantitative single-molecule analysis.

Detailed Protocol

1. The following oligo was resuspended in 1× Microspotting solution (ArrayIt):

```
5Am12-ctgac
/5AmMC12/TTTTTTTTTT/ideoxyU//ideoxyU/
CTACACTCTTTCCCTACACGACGCTCTTCCGATCT CTGAC (SEQ ID
NO: 4)
```

2. One aldehyde coated slide was spotted with the above oligo mix. The slide was then incubated at 60° C. for 1 hour.

3. The slide was then washed once with water, once with 0.1% SDS+1 mM TrisHCl, and three more times in with water.

4. To reduce the Schiff bases and unreacted aldehydes, a solution of 0.15 g $NaBH_4$ in 35 mL PBS was prepared. After $NaBH_4$ was dissolved, 15 mL 100% was added to the solution. The slide was incubated in this solution for 15 minutes.

5. To denature DNA, the slide was incubated in ~80° C. water for three minutes and then submerged in ice-cold 100% ethanol for thirty seconds (last sequence to denature the oligos and keep them that way).

6. Slide was dried by centrifugation at 500 g for 3 minutes.

7. 0, 15.625, 31.25, 62.5, 125, 250, 500, and 1000 uM dilutions of 7-deaza-7-bromo-dATP, 7-propynyl-dUTP, dCTP, and dGTP in 25% ethanol were prepared.

8. A 2 µl droplet of each nucleotide concentration was printed on an oligo spot with a liquid handling robot and then dried at room temperature (RT) for a few minutes.

9. A 5 µl droplet of this enzymatic mix was deposited on each spot with dried nucleotide:
15 mM Tris-Acetate, 35 mM Potassium Acetate, 7 mM Magnesium Acetate, 1 U/µL TdT enzyme, 0.001 U/µL Apyrase enzyme, pH=8.0.

10. After 4 minutes of incubation at room temperature, the slide was washed with room temperature 0.1% SDS once and water twice, and then dried again with centrifugation.

11. Ligation was carried out on the slide overnight at room temperature with the following mix:
50 mM Tris-HCl, 10 mM $MgCl_2$, 1 mM DTT, 1 mM ATP, 25% PEG 8K, 1 µM 5P-cagtc oligo, 0.8 U/µ1 T4 RNA ligase 1, pH=7.5
where the oligo 5P-cagtc has the following sequence:

```
                                        (SEQ ID NO: 5)
/5phos/CAGTC AGATCGGAAGAGCACACGTCTGAACTCCAGTCA
```

12. Ligation mix was washed by 0.1% SDS wash and two washes with water. The slide was dried by centrifugation.

13. Samples were eluted once using 1.0 ul USER mix at 37 C for 30 minutes:
10 mM Tris-HCl pH=8, 0.2 U/µL UDG enzyme, 0.5 U/µL Endonuclease VIII enzyme 14. 2 µL of each template was amplified in a reaction with S1 and S2 as primers.

```
S1 CTACACTCTTTCCCTACACGAC (SEQ ID NO: 6)

S2 GTGACTGGAGTTCAGACGTG (SEQ ID NO: 7)
```

15. 5 µL of each PCR product was run on a 4% Agarose gel (as shown in FIG. 6).

These results illustrated that Apyrase effectively limited the average amount of extension by TdT in each reaction. Furthermore, the amount of nucleotide used in the reaction can be used to adjust the amount of these extensions.

16. 0.5 µl of the PCR product was used in a second PCR with NEBNext Dual Indexing Primer Set and sequenced on an Illumina MiSeq with 100 bp single read.

Figure 7:
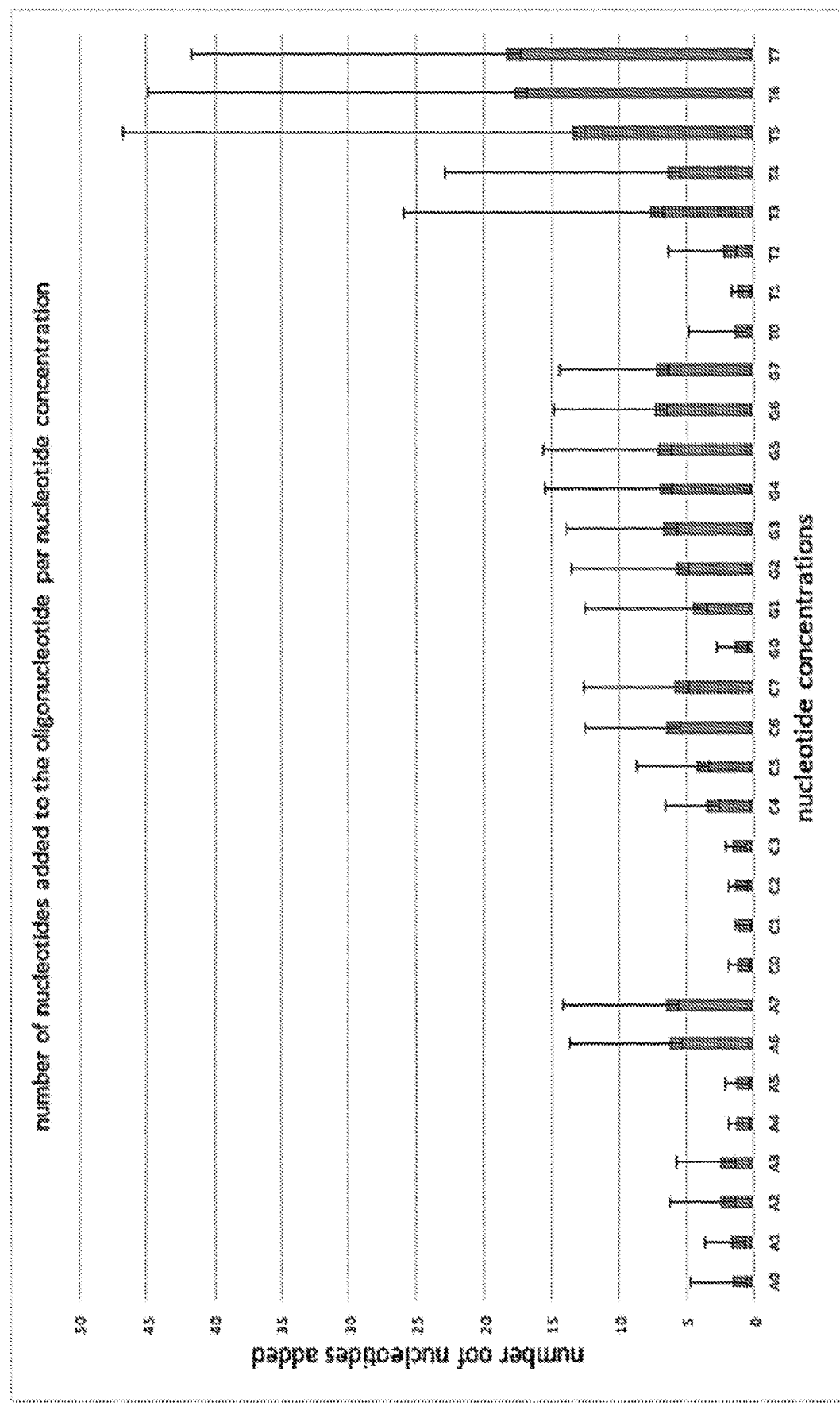
FIG. 7 depicts quantification of the number of nucleotides added to the oligonucleotide initiator for each nucleotide type and concentration in addition to the number of oligonucleotide initiators that received nonzero addition of nucleotides for each nucleotide type and concentration according to the embodiments of the disclosed methods and as measured by high-throughput single-molecule sequencing.
Figure 8:
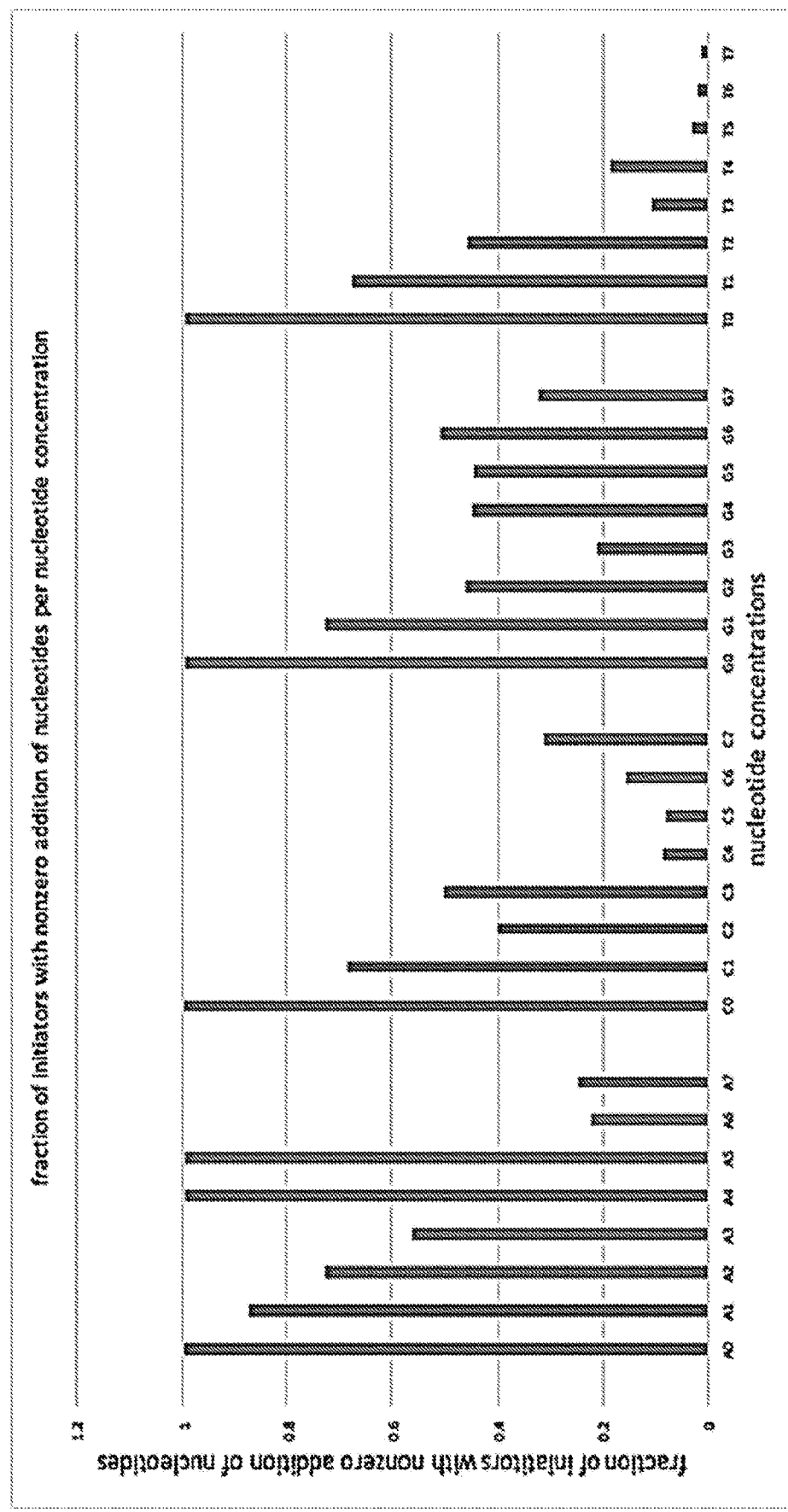
FIG. 8 depicts fraction of initiators with nonzero addition of nucleotides per nucleotide concentration according to the embodiments of the disclosed methods.
Figure 9:
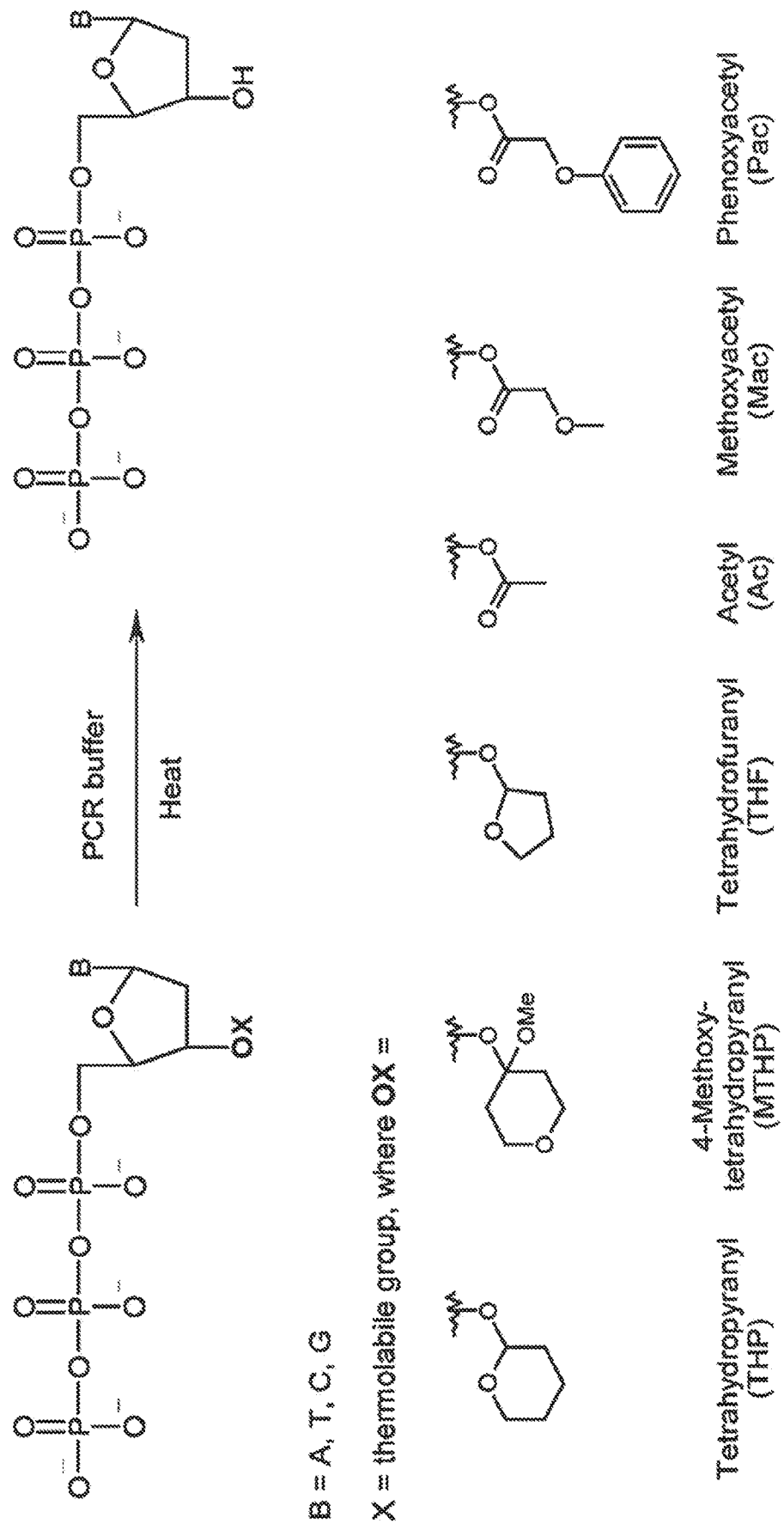
FIG. 9 depicts 3'-modified reversible terminators.
Figure 10:
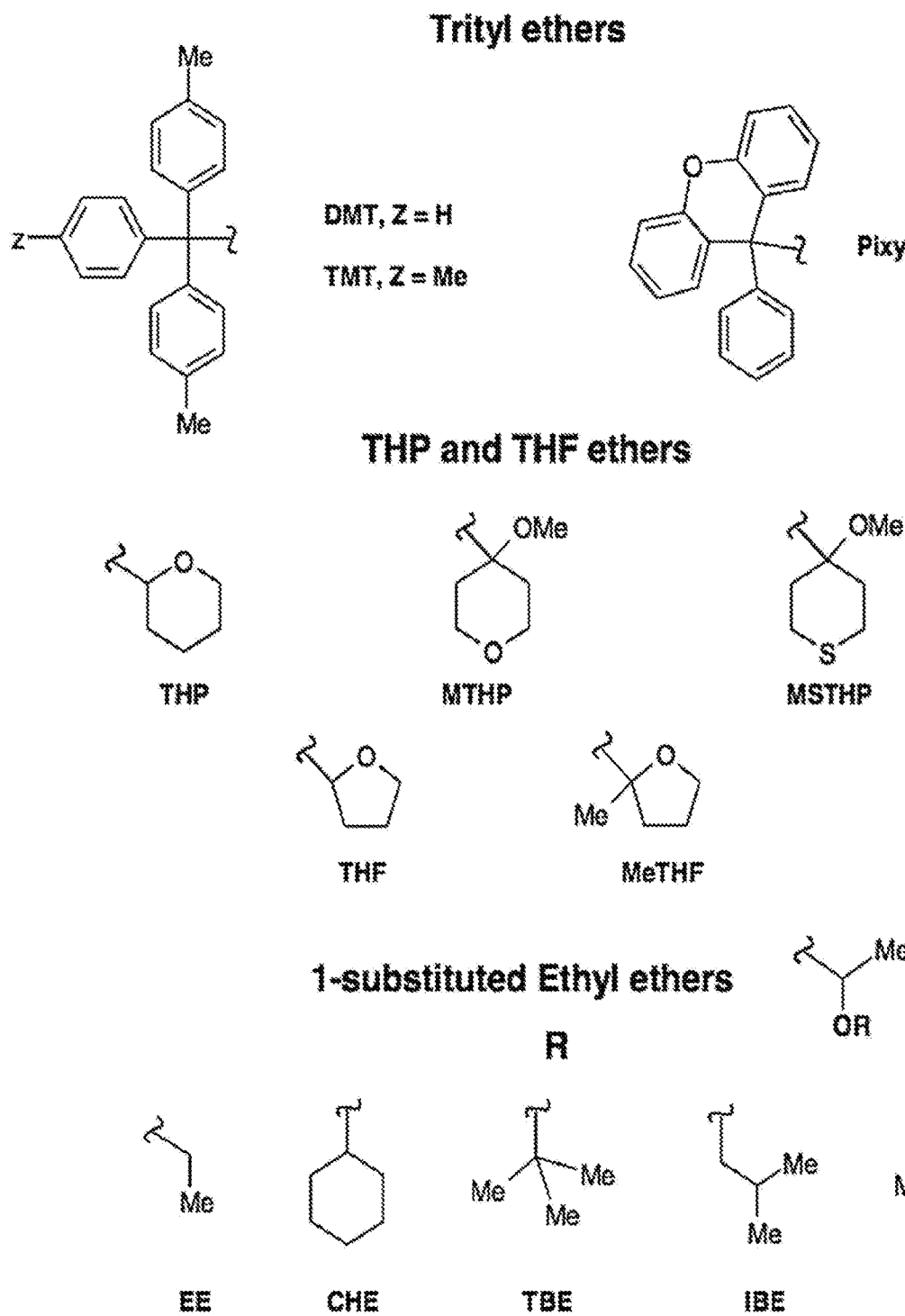
FIG. 10 depicts 3'-modified reversible terminators.
Figure 11:
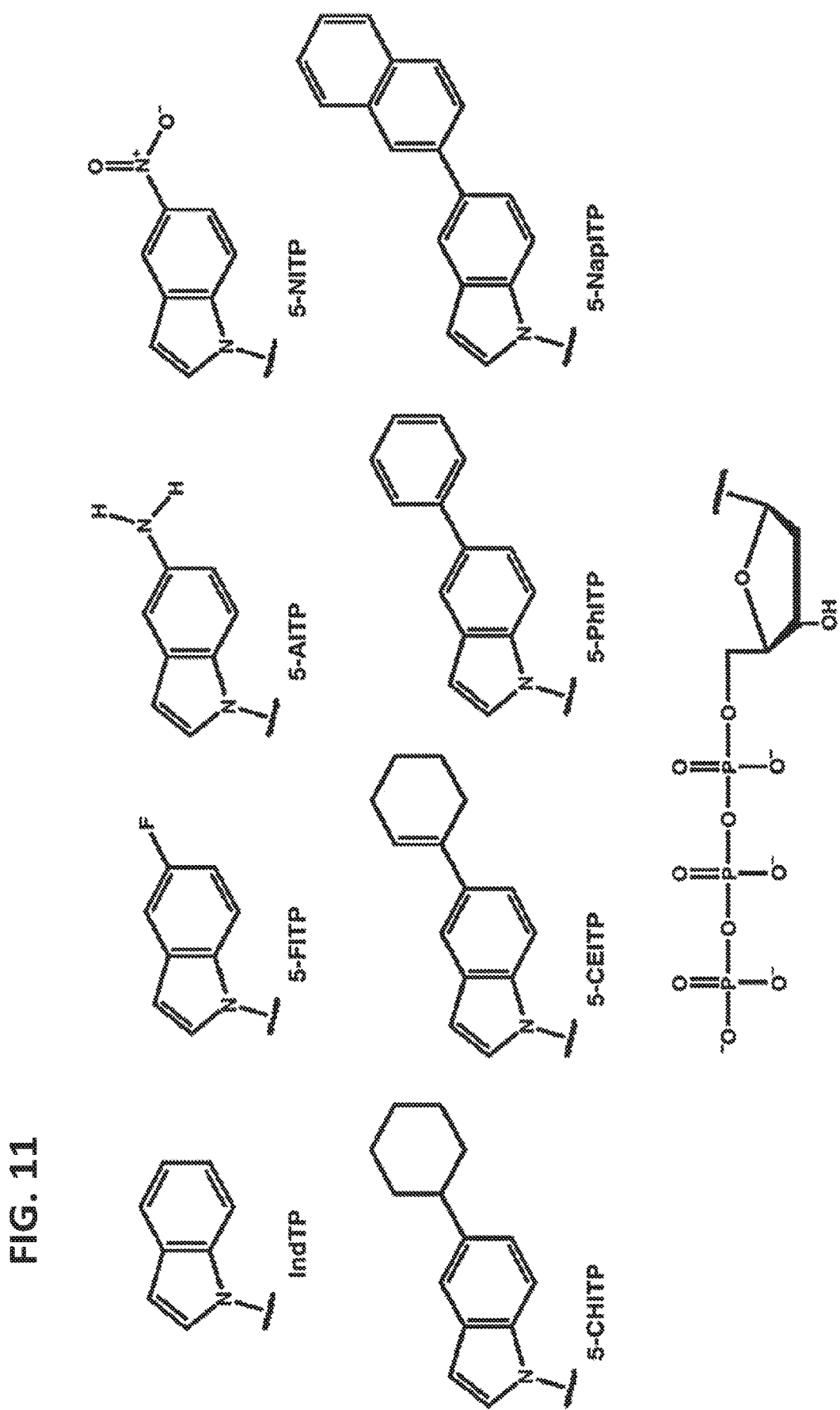
FIG. 11 depicts base-modified nucleotides.

Based on analysis of Illumina MiSeq reads, the number of nucleotides added to the oligonucleotide initiator were quantified for each nucleotide type and concentration in addition to the number of oligonucleotide initiators that received nonzero addition of nucleotides for each nucleotide type and concentration (See, FIG. 7 and FIG. 8), where 0 to 7 for each base (i.e. A0 to A7) corresponds to increasing concentrations of a given nucleotide.

Modulating the TdT Enzymatic Activity by pH

The objective of these experiments is to determine the range of pH in which TdT is active.

1. A buffer of 50 mM Tris (base) and 50 mM Boric acid was prepared and its pH (initially at ~8.5) was adjusted to 6.05, 6.9, 7.93, 8.96, 10.02, and 11.07 using acetic acid and sodium hydroxide. These buffers serve as 2× buffers in the experiments.

2. Extension reactions were assembled as follows:
Water: 5 µl
2× Buffer: 10 µl
25 µM initiator: 1 µl
100 mM $MgSO_4$ or water: 2 µl
1 mM dCTP: 1 µl
TdT (20 U/µl): 1 µl
Total Volume: 20 µl 3. Each reaction was incubated for 15 minutes and then loaded on a TBE-Urea gel with an unextended initiator for comparison.

Figure 13:
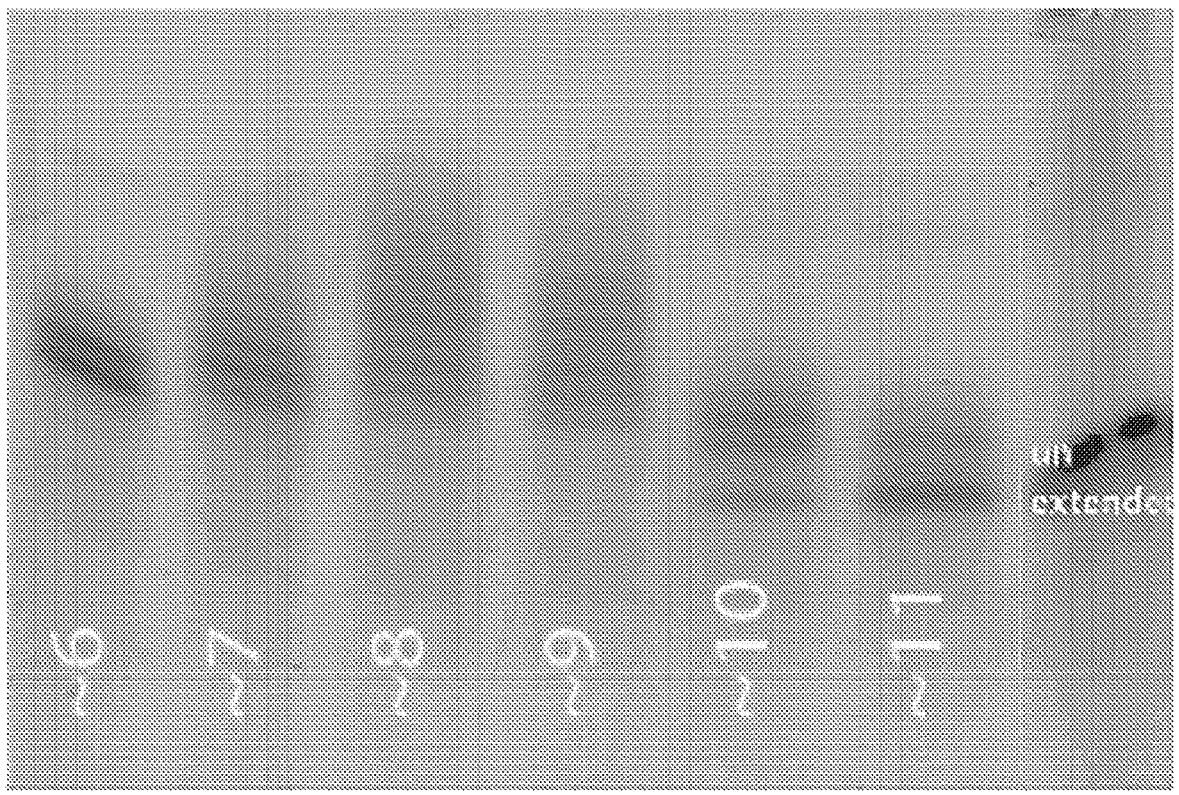
FIG. 13 depicts results for pH regulation of TdT enzyme activity on a TBE-Urea gel according to the embodiments of the disclosed methods.

As shown in FIG. 13, the results in the TBE-Urea gel established that pH can be used to regulate the activity of TdT enzyme in a way that is adaptable for pH-based TdT-control for data storage. It also needs to be established that the effects of pH on TdT are reversible; that is, the enzyme's activity can be substantially reduced at an unfavorable pH but can be reverted back to normal activity at favorable pH. The ensuing experiment was performed to evaluate this question.

In the following experiment, TdT was incubated at a pH for 15 minutes without the nucleotide or the initiator, it was then combined with the nucleotide and the initiator in such a way that the final pH of the mixture during polymerization would be different from that of the initial 15 min incubation.

1. A buffer of 50 mM Tris (base) and 50 mM Boric acid was prepared and its pH (initially at ~8.5) was adjusted to 6.05, 6.9, 7.93, 8.96, 10.02, and 11.07 using acetic acid and sodium hydroxide. These buffers serve as 2× buffers in the experiment.

2. Extension reactions were assembled in two parts:
Part 1:
Water: 5 µl
2× Buffer: 5 µl
100 mM MgAc: 2 µl
TdT (20 U/µl): 1 µl
Total Volume: 10 µl
Part 2:
Water: 3 µl
2× Buffer: 5 µl
25 µM initiator: 1 µl
1 mM dCTP: 1 µl
Total Volume: 10 µl
Eight different extension reactions were assembled with following pH used for the buffer in part 1 and part 2:

| Reaction | | | | | | | | | |
|---|---|---|---|---|---|---|---|---|---|
| | A | B | C | D | E* | F | G | H | I |
| Part 1 Buffer | 6 | 6 | 6 | 8 | 6 + 11 | 9 | 11 | 11 | 11 |
| Part 2 Buffer | 6 | 10 | 11 | 8 | 6 + 11 | 9 | 6 | 7 | 11 |

Figure 14:
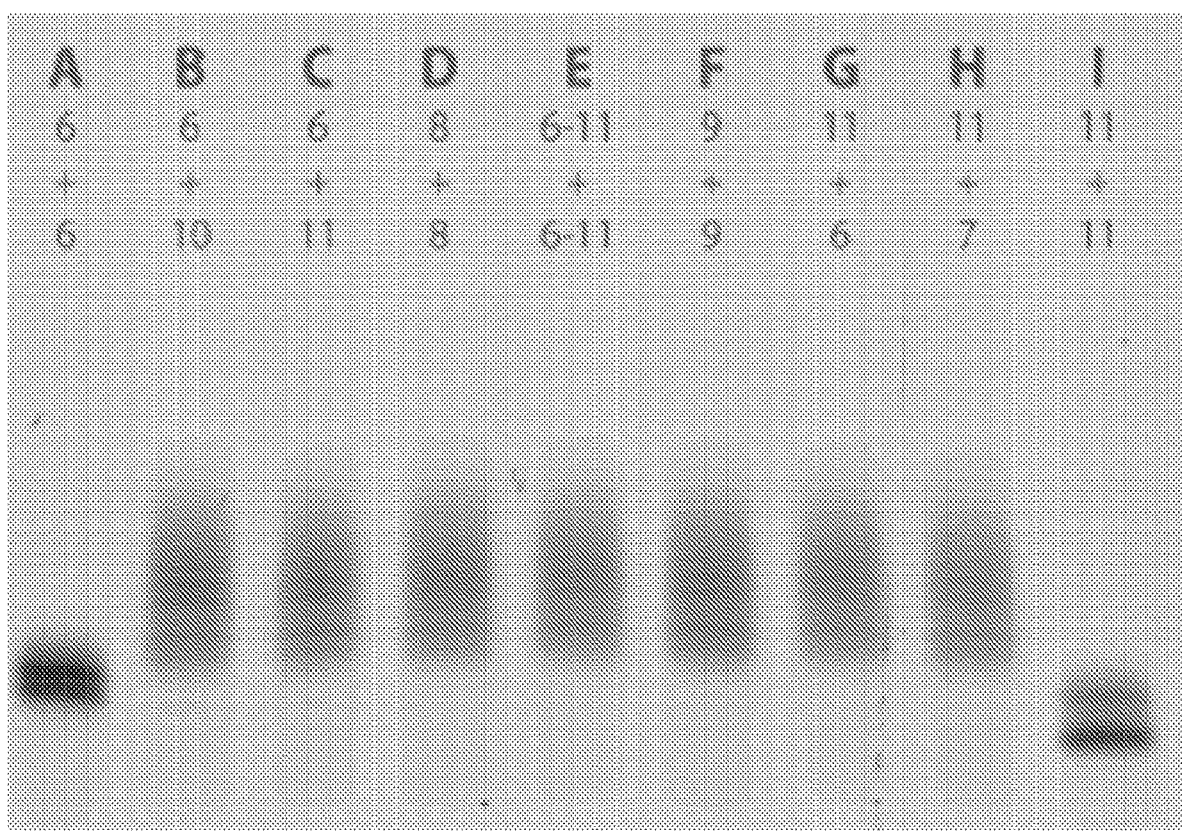
FIG. 14 depicts results for reversible pH regulation of TdT enzyme activity on a TBE-Urea gel according to the embodiments of the disclosed methods.

3. Both parts of each reaction were incubated for 15 minutes, they were then mixed to form the 20 µl total, then loaded on a TBE-Urea gel:

As shown in FIG. 14, TdT is highly active in pH ranges that are above 6 and below 11, and it is substantially inactivated at pH ranges that are below 6 and above 11. It was clear from this experiment that the enzymatic activity of TdT could be reversibly inhibited by both increasing and reducing the pH. Inhibition of TdT enzymatic activity was more effective at pH~11 than it was at pH~6.

For example, as shown in FIG. 14 in lanes A and I, the starting pH was 6 and 11 respectively where the enzyme showed little to no polymerization activity. Lanes B and C showed that when the enzyme was kept at pH=6 it could be activated by increasing the pH to more alkaline values. Lanes G and H showed that when the enzyme was kept at pH=11, it could be activated by decreasing the pH to more acidic values. Since the enzyme apparently did not denature irreversibly at either pH=6 or pH=11, it was clear that the effect of pH on the enzymatic activity was reversible and the enzyme could be activated and inactivated multiple times by changing the pH. Therefore, it has been demonstrated that TdT could be reversibly inactivated by changing the pH of the reaction solution to 11 or above. Specifically, the enzyme was highly active in pH from 6 to 10 and largely inactive at pH greater than 11 but could be reactivated once the pH is lowered back within 6-10 range.

Figure 15:
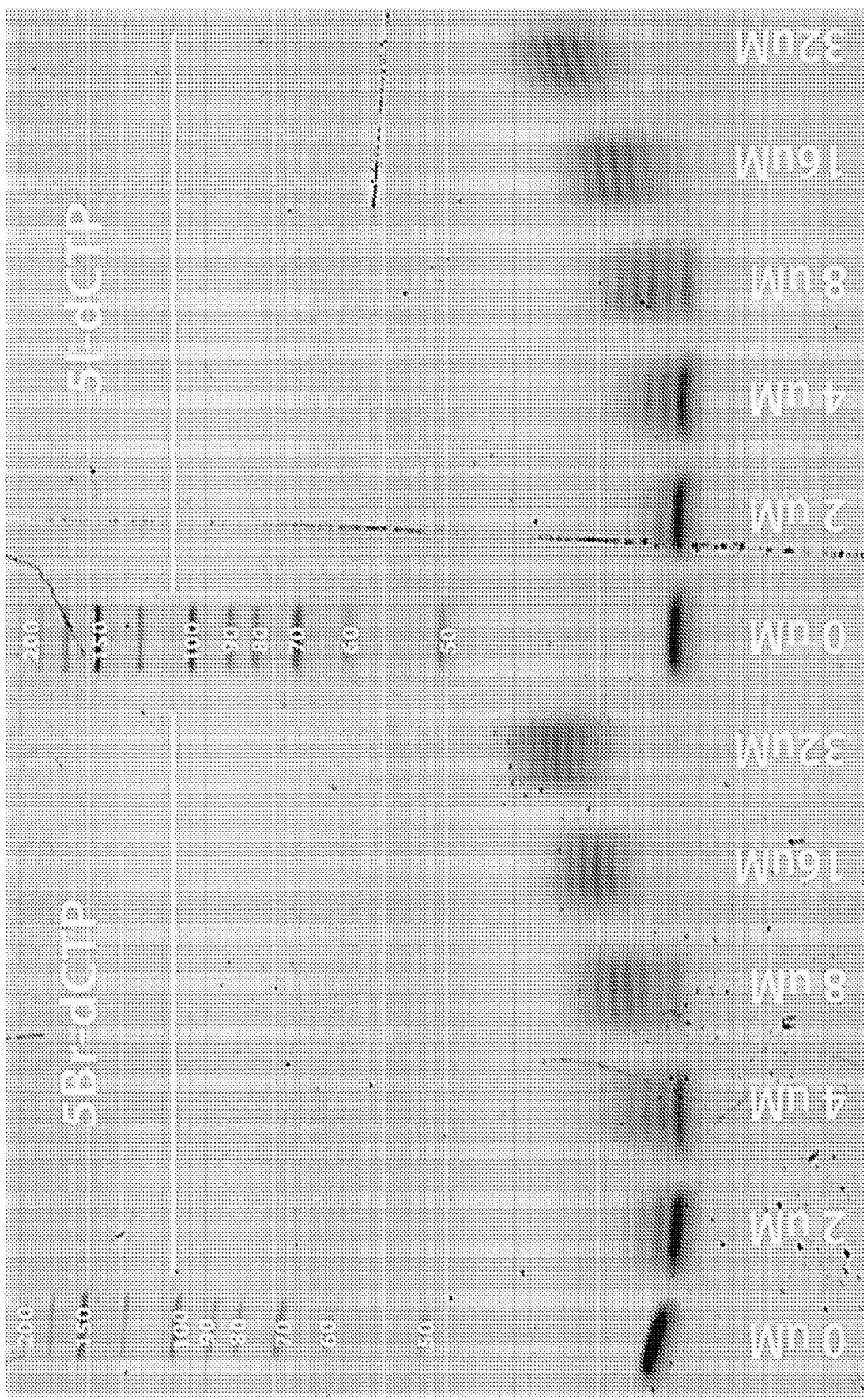
FIG. 15 is a gel image showing results for 5BR-dCTP and 5I-dCTP.
Figure 16:
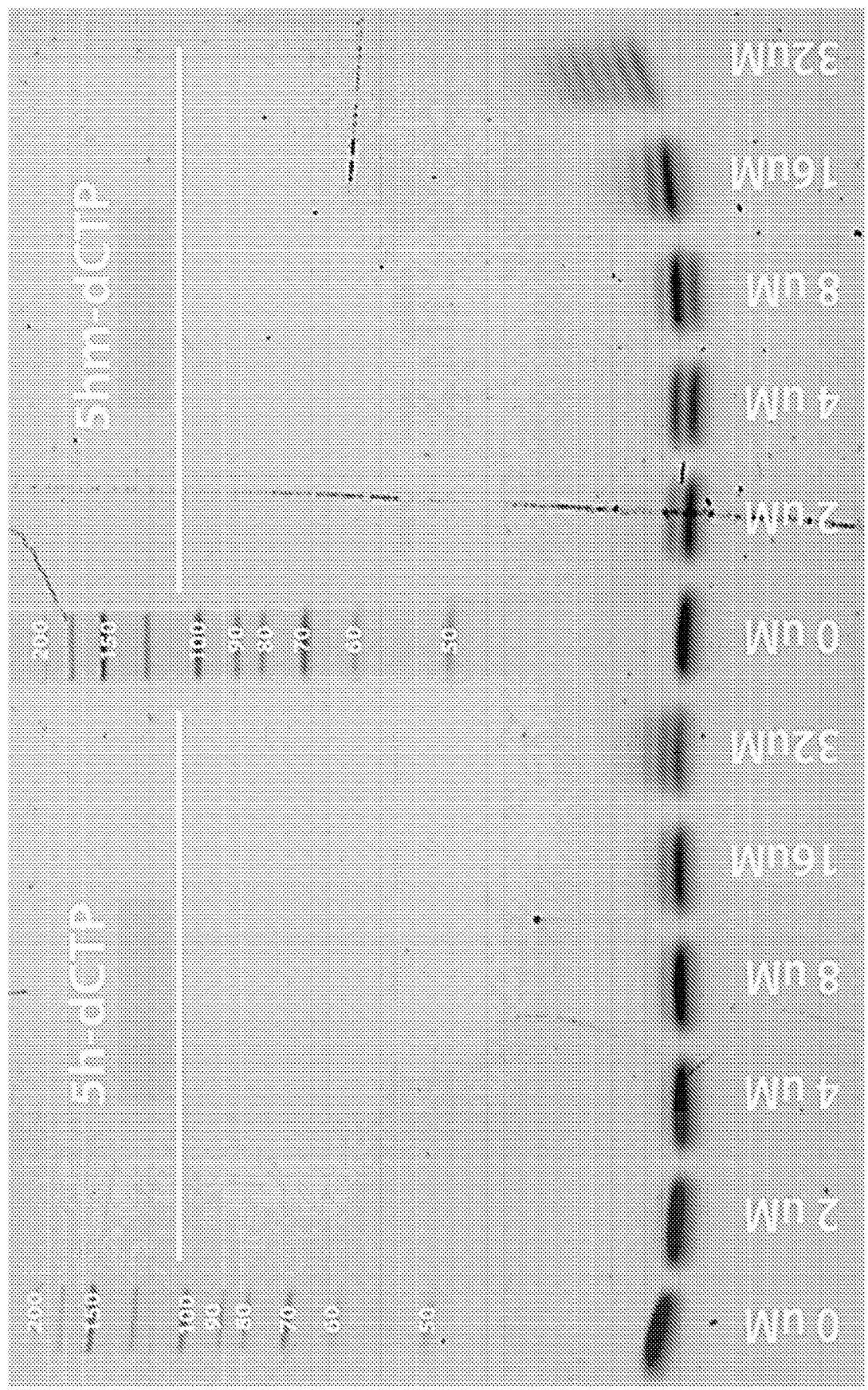
FIG. 16 is a gel image showing results for 5h-dCTP and 5hm-dCTP.
Figure 17:
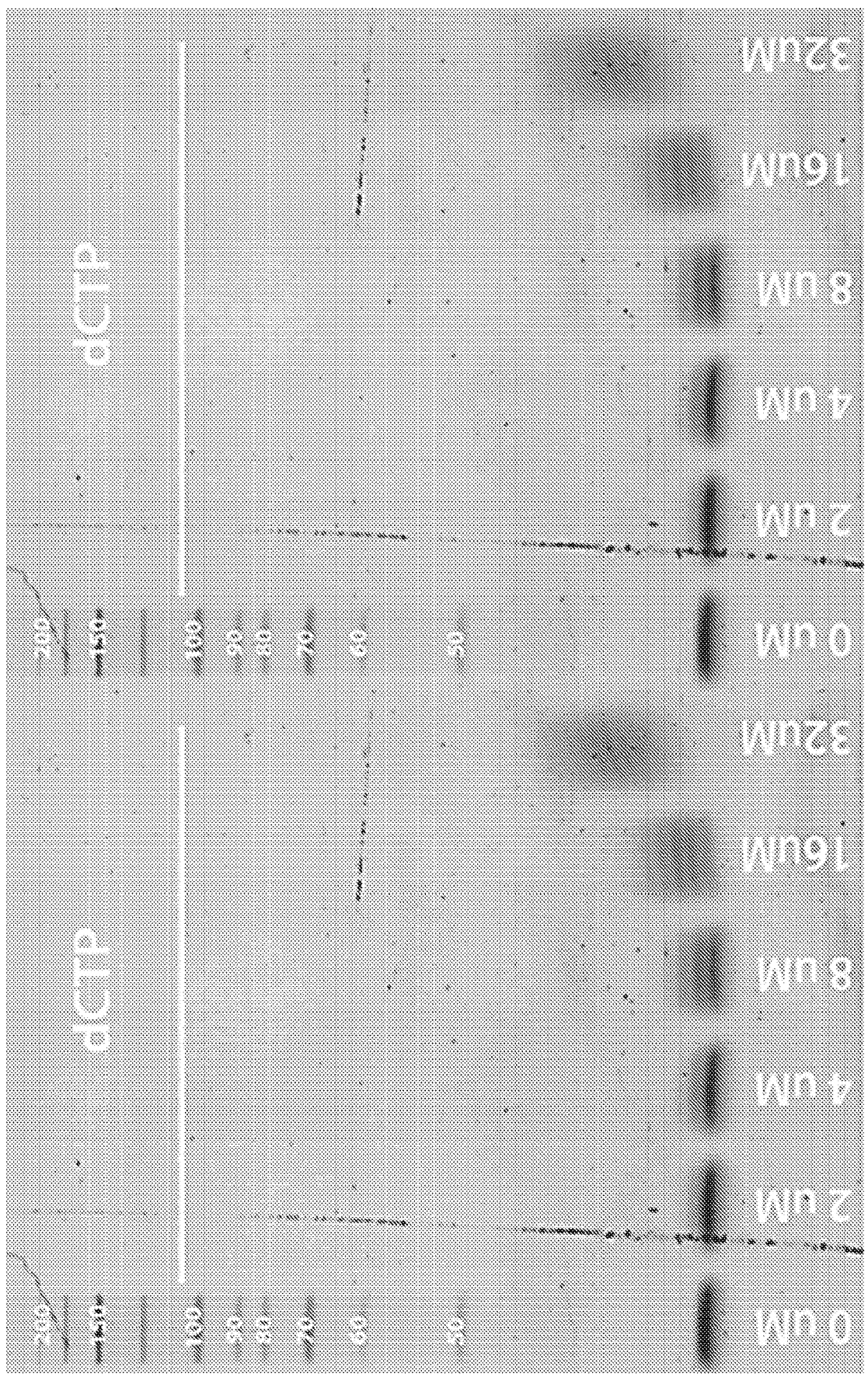
FIG. 17 is a gel image showing results for 5m-dCTP and dCTP.

The following modified nucleotide analogues were tested with an initiator oligonucleotide: 5-Hydroxy-dCTP (hdCTP), 5-Hydroxymethyl-dCTP (hmdCTP), 5-Bromo-dCTP (BrdCTP), 5-Iodo-dCTP (IdCTP) and 5-methyl-dCTP (5m-dCTP). Nucleotides and their respective final concentrations to be used are hdCTP: 0, 2, 4, 8, 16, 32 uM; hmdCTP: 0, 2, 4, 8, 16, 32 uM; BrdCTP: 0, 2, 4, 8, 16, 32 uM; IdCTP: 0, 2, 4, 8, 16, 32 uM; and 5mdCTP: 0, 2, 4, 8, 16, 32 uM. The reaction stop solution, STOP&LOAD, was prepared as 20 ul Novex 2×TBE-Urea loading buffer containing 20 mM EDTA. For each reaction, a 16 ul reaction solution was prepared as follows as a mastermix: 3 µl Water; 10 µl 2× Reaction Buffer; 2 µl 1 uM Primer; 1 µl TdT enzymatic mix; for a total volume of 16 ul. Each reaction was then mixed with the following components in the specified order: dNTP (various 4× concentrations) at 4.0 µl. All reactions were carried out at 22° C. For each reaction, 16 ul of the reaction mix was mixed with 4.0 ul of dNTP. After 5 minutes of incubation, 20 ul of STOP&LOAD was mixed with the reaction. All samples were incubated at 75° C. for 5 minutes and cooled down on ice. 9 ul of each loading mix was loaded on a 15% TBE-Urea gel. Gel was run in 1×TBE at 180V for 90 minutes. After running, the gel was stained in 1× SybrGold in 1×TBE for 15 minutes, rinsed once with 1×TBE, and imaged on the GelDoc with 5 second exposure in the SybrGold channel. FIG. 15 is a gel image showing results for 5BR-dCTP and 5I-dCTP. FIG. 16 is a gel image showing results for 5h-dCTP and 5hm-dCTP. FIG. 17 is a gel image showing results for 5m-dCTP and dCTP.

OTHER EMBODIMENTS

Other embodiments will be evident to those of skill in the art. It should be understood that the foregoing description is provided for clarity only and is merely exemplary. The spirit and scope of the present invention are not limited to the above examples, but are encompassed by the following claims. All publications and patent applications cited above are incorporated by reference in their entirety for all purposes to the same extent as if each individual publication or patent application were specifically and individually indicated to be so incorporated by reference.

The invention claimed is:

1. A method for making a polynucleotide comprising
   (a) combining a selected nucleotide triphosphate, cations, a template independent DNA polymerase, and a nucleotide triphosphate inactivating enzyme at a reaction site on a support surface including an initiator sequence attached thereto and having a 3' terminal nucleotide, wherein reaction reagents are present at selected concentrations and under conditions which covalently add one or more of the selected nucleotide triphosphate to the 3' terminal nucleotide such that the selected nucleotide triphosphate becomes a 3' terminal nucleotide and under conditions which inactivate free nucleotide triphosphates until free nucleotide triphosphates are substantially inactivated, wherein a desired number of the selected nucleotide triphosphate is added to the initiator sequence, and
   (b) repeating step (a) until the polynucleotide is formed.

2. The method of claim 1 wherein the nucleotide triphosphate inactivating enzyme is a nucleotide triphosphate degrading enzyme.

3. The method of claim 1 wherein the nucleotide triphosphate inactivating enzyme is a nucleotide triphosphate degrading enzyme that degrades nucleotide triphosphates at a rate slower than rate of addition of nucleotides by the template independent DNA polymerase.

4. The method of claim 1 wherein the nucleotide triphosphate inactivating enzyme is a nucleotide triphosphate degrading enzyme present at a concentration that degrades nucleotide triphosphates at a rate slower than rate of addition of nucleotides by the present concentration of the template independent DNA polymerase.

5. The method of claim 1 wherein the nucleotide triphosphate inactivating enzyme comprises ATP diphosphohydrolase, dNTP pyrophosphatases, dNTPases, and phosphatases.

6. The method of claim 1 wherein the concentration of nucleotide triphosphate inactivating enzyme is modulated to control addition of one or more nucleotides.

7. The method of claim 1 wherein the nucleotide triphosphate inactivating enzyme renders free nucleotide triphosphates inactive by degradation.

8. The method of claim 1 wherein the nucleotide triphosphate inactivating enzyme renders free nucleotide triphosphates inactive by polymerizing them with each other.

9. The method of claim 1 wherein the selected nucleotide triphosphate is added to the reaction site on the support surface including the initiator sequence having the terminal nucleotide, the template independent DNA polymerase and the nucleotide triphosphate inactivating enzyme.

10. The method of claim 1 wherein the template independent DNA polymerase and the nucleotide triphosphate inactivating enzyme are added to the reaction site on the support surface including the initiator sequence having the terminal nucleotide, and the selected nucleotide triphosphate.

11. The method of claim 10 wherein the reaction reagents are removed from the reaction site on the support surface and additional reaction reagents are provided to the reaction site on the support surface after each round of addition.

12. The method of claim 1 wherein the nucleotide triphosphate inactivating enzyme is added to the reaction site on the support surface including the initiator sequence having the terminal nucleotide, the template independent DNA polymerase and the selected nucleotide triphosphate under conditions where the polymerase is inactive, and wherein the polymerase is activated upon addition of the nucleotide triphosphate inactivating enzyme.

13. The method of claim 12 wherein the reaction reagents are removed from the reaction site on the support surface and additional reaction reagents are provided to the reaction site on the support surface after each round of addition.

14. The method of claim 1 wherein step (b) is repeated a plurality of times after which the reaction reagents are removed from the reaction site on the support surface and additional reaction reagents are provided to the reaction site on the support surface.

\* \* \* \* \*

SEQUENCE LISTING

```
<160> NUMBER OF SEQ ID NOS: 8

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
aaattaaccc cggacttaag ggcc                                          24

<210> SEQ ID NO 2
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
atacgactag c                                                        11

<210> SEQ ID NO 3
<211> LENGTH: 50
```

```
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: misc_feature
<222> LOCATION: (1)..(50)
<223> OTHER INFORMATION: This sequence may encompass 4-50 nucleotides

<400> SEQUENCE: 3
aaaaaaaaaa aaaaaaaaaa aaaaaaaaaa aaaaaaaaaa aaaaaaaaaa              50

<210> SEQ ID NO 4
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: 5'-5AmMC12
<220> FEATURE:
<221> NAME/KEY: modified_base
<222> LOCATION: (11)..(12)
<223> OTHER INFORMATION: ideoxyU

<400> SEQUENCE: 4
tttttttttt uuctacactc tttccctaca cgacgctctt ccgatctctg ac            52

<210> SEQ ID NO 5
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-Phos
<220> FEATURE:
<221> NAME/KEY: modified_base
<222> LOCATION: (39)..(39)
<223> OTHER INFORMATION: 3ddC

<400> SEQUENCE: 5
cagtcagatc ggaagagcac acgtctgaac tccagtcac                           39

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ctacactctt tccctacacg ac                                             22

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
```

```
gtgactggag ttcagacgtg                                                      20

<210> SEQ ID NO 8
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (31)..(32)
<223> OTHER INFORMATION: ideoxyU

<400> SEQUENCE: 8
tttttttttt tttttttttt tttttttttt uucgacgctc ttccgatctc tgac             54
```